(12) United States Patent
Richey

(10) Patent No.: US 10,166,044 B1
(45) Date of Patent: Jan. 1, 2019

(54) APPARATUS FOR REPOSITIONING THE VAGINA, CERVIX, UTERUS AND PELVIC FLOOR AND METHOD TO SECURE SAME

(71) Applicant: Mark Edmund Richey, Anchorage, AK (US)

(72) Inventor: Mark Edmund Richey, Anchorage, AK (US)

(73) Assignee: FRESHWATER BAY INDUSTRIES, LLC, Anchorage, AK (US)

( * ) Notice: Subject to any disclaimer, the term of this patent is extended or adjusted under 35 U.S.C. 154(b) by 802 days.

(21) Appl. No.: 13/852,784

(22) Filed: May 31, 2013

(51) Int. Cl.
*A61B 17/42* (2006.01)

(52) U.S. Cl.
CPC .................... *A61B 17/42* (2013.01)

(58) Field of Classification Search
CPC .............. A61M 29/00; A61B 90/03; A61B 2017/4225; A61B 1/303; A61B 17/4241; A61B 17/42; A61B 17/12099
USPC .............................................. 606/193; 600/37
See application file for complete search history.

(56) References Cited

U.S. PATENT DOCUMENTS

| | | | |
|---|---|---|---|
| 1,940,122 A * | 12/1933 | Gardner | A61B 17/42 601/161 |
| 3,587,588 A * | 6/1971 | Murr | 606/191 |
| 4,022,208 A | 5/1977 | Valtchev | |
| 4,198,982 A * | 4/1980 | Fortner | A61B 17/115 227/179.1 |
| 4,710,075 A | 12/1987 | Davison | |
| 4,877,037 A | 10/1989 | Ko | |
| 5,409,496 A | 4/1995 | Rowden | |
| 5,421,346 A * | 6/1995 | Sanyal | 600/563 |
| 5,792,053 A | 8/1998 | Skladnev et al. | |
| 8,292,901 B2 | 10/2012 | Auerbach | |
| 8,460,209 B2 | 6/2013 | Klein | |
| 8,976,363 B2 | 3/2015 | Bendall et al. | |
| 2003/0187334 A1 | 10/2003 | Biswas | |
| 2005/0137557 A1* | 6/2005 | Swiecicki et al. | 604/385.17 |
| 2007/0100201 A1 | 5/2007 | Komiya et al. | |
| 2008/0221590 A1 | 9/2008 | Ikeda | |
| 2009/0069634 A1 | 3/2009 | Larkin et al. | |
| 2009/0204126 A1 | 8/2009 | Le | |
| 2010/0106163 A1 | 4/2010 | Blair | |
| 2012/0016185 A1 | 1/2012 | Sherts | |

(Continued)

*Primary Examiner* — Christine H Matthews
(74) *Attorney, Agent, or Firm* — Ruttler Mills, PLLC; James J. Ruttler

(57) ABSTRACT

This invention relates to the pelvic floor and vagina manipulator probes and related systems and methods. In certain aspects of the invention, a vaginal manipulator probe assembly is comprised of an intravaginal body curved along its long axis and with an adjustable pelvic floor ring. The probe assembly can be configured as an apparatus for insertion into a vagina for repositioning the vagina, cervix, uterus and pelvic floor and method for securing the same. In certain aspects, the curved intravaginal probe can be configured to receive a cervix. In certain implementations, the vaginal manipulator probe facilitates surgical visibility, dissection, and graft placement, is a device to elevate, support, and expose the pelvic floor and perineal body during surgical repair, is a device to set the proper vaginal insertion depth, is a device to assist with proper tensioning of the repositioned pelvic floor structures, and is a device to facilitate shortening of the anterior or posterior vaginal wall.

20 Claims, 28 Drawing Sheets

(56) References Cited

U.S. PATENT DOCUMENTS

| | | |
|---|---|---|
| 2012/0203244 A1* | 8/2012 | McDonald et al. .......... 606/119 |
| 2012/0226101 A1 | 9/2012 | Tinkham et al. |
| 2012/0289585 A1 | 11/2012 | Ouyang |
| 2013/0072749 A1 | 3/2013 | Fairneny |
| 2013/0197537 A1 | 8/2013 | Fairneny |
| 2015/0005780 A1* | 1/2015 | Einarsson .................... 606/119 |
| 2015/0351621 A1 | 12/2015 | Hill et al. |
| 2017/0319047 A1 | 11/2017 | Poulsen et al. |

* cited by examiner

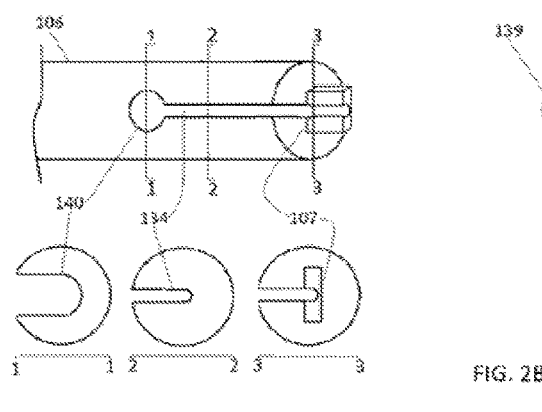
FIG. 2B
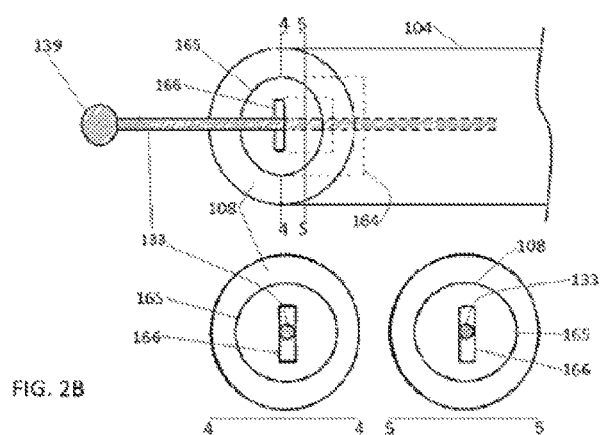

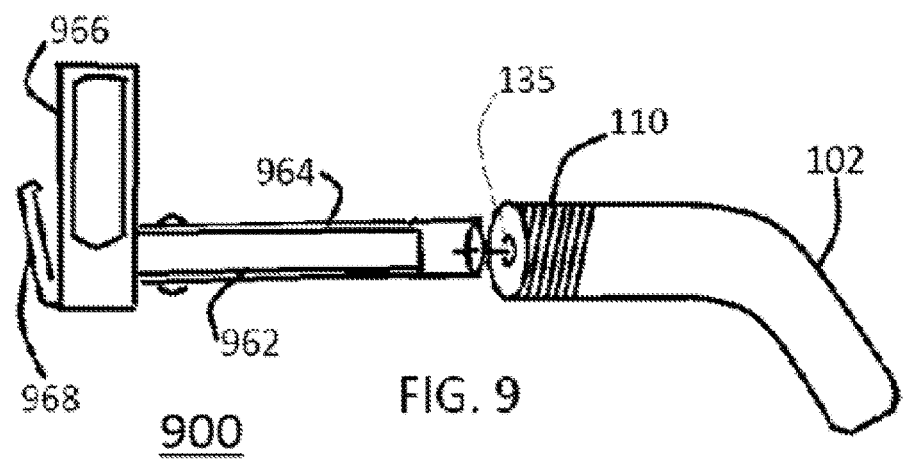

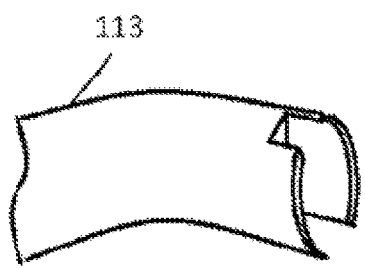
FIG. 13
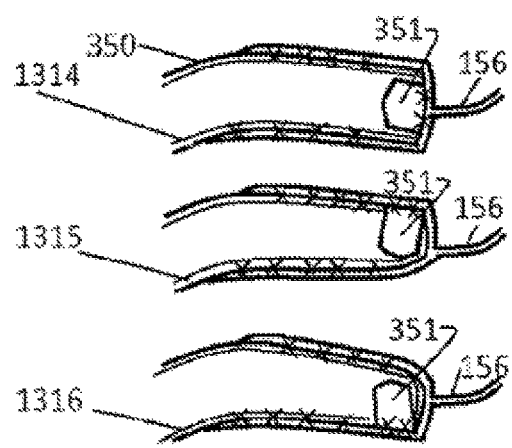

APPARATUS FOR REPOSITIONING THE VAGINA, CERVIX, UTERUS AND PELVIC FLOOR AND METHOD TO SECURE SAME

CROSS REFERENCE TO RELATED APPLICATIONS

Not Applicable

STATEMENT REGARDING FEDERALLY SPONSORED RESEARCH OR DEVELOPMENT

Not Applicable

DESCRIPTION OF ATTACHED APPENDIX

Not Applicable

BACKGROUND OF THE INVENTION

This invention relates generally to the field of surgical devices and more specifically to an apparatus for repositioning the vagina, cervix, uterus and pelvic floor and method for securing same.

Women may have weakened or damaged pelvic floor muscles, connective tissue, ligaments and skin, often related to past pregnancy and childbirth or genetic factors. The weakened or damaged connective tissue, muscles and ligaments fail to provide adequate support to the vagina, cervix, uterus and pelvic floor, which may lead to excessive movement of these structures and a falling away from their normal position in the body in a condition called uterovaginal prolapse or pelvic prolapse, causing symptoms and dysfunction of the related organs. One type of prolapse of the vagina and pelvic floor may involve a weakened anterior vaginal portion, which normally supports the bladder, causing the anterior vaginal wall, bladder and ureters to be displaced downward toward, or out through, the vaginal opening. Another type of prolapse involves the apical portion, which is the deepest "inside" or top portion of the vagina, and the cervix with uterus, if present. Many women may have previously had a hysterectomy, with removal of the uterus and/or cervix, which predisposes them to vaginal prolapse. The apical portion of the vagina, with uterus and cervix, if present, may descend toward or out through the vaginal opening. Another type of prolapse involves the posterior vaginal wall and rectum, which may descend downward toward, or out through, the vaginal opening. Another type of prolapse involves the perineal body, a pyramid-shaped structure between the most distal portion of the vagina and anus, which may become weakened and detached from its supporting connective tissue, muscles, ligaments, or skin, resulting in excessive movement of the perineal body and entire pelvic floor. Each of these types of prolapse may occur singly or together in any combination.

Pelvic floor prolapse can be corrected with certain types of surgery, such as vaginal procedures, open abdominal (laparotomy), or "closed" abdominal laparoscopic techniques. In the early twentieth century, repair of the anterior vaginal compartment (anterior colporrhaphy for repair of cystocele) and/or repair of the posterior vaginal compartment (posterior colporrhaphy for repair of rectocele) were offered to women with prolapse in these areas. The repair procedures comprised techniques performed through the vaginal opening, which resulted in a reduction in excess vaginal length and girth. High rates of recurrence and disabling prolapse, pain or scarring sometimes followed these procedures. In 1957, surgeons began attaching the uterus to the anterior longitudinal ligament as a more durable technique. In 1962, Lane first described the use of a bridging material, or graft, to attach the vagina and cervix to the sacrum via an open abdominal, or laparotomy procedure, to support the apical compartment of the vagina. Slow recovery and morbidity often followed as a result of the large abdominal incision for this procedure.

With advances in surgical equipment and technique, many of these repairs are now performed laparoscopically, utilizing several small incisions in the abdominal wall. The surgical treatment usually involves a technique where the surgeon attaches the cervix, vagina, and/or perineal body muscles and connective tissue via a graft material to the strong ligamentous structure overlying the sacral promontory at the base of the spine. The procedure is termed sacrocolpopexy.

A vaginal manipulator device which became available around 2010 as described in the U.S. Patent Application Publication No. 2012/0016185 A1 has a number of deficiencies. First, the manipulator tip intravaginal portion is straight along its long axis which often does not allow adequate exposure for surgical dissection and placement of sutures for the anterior wall under the bladder, or for the posterior vaginal wall, extending down to the perineal body and pelvic floor, which is the optimal technique. The optional external curved handle, or other available handles, do not compensate for this deficiency, and therefore this tip compromises the surgical technique, safety and efficiency of the sacrocolpopexy procedure. Secondly, although the distal tip portion of the vaginal manipulator can have a recess for the cervix to be received, or other annular, bladed-type systems as described, none of these provide for the cervix to be repositioned in an anterior or posterior orientation, and therefore do not allow for cystocele and/or rectocele reduction by shortening of the anterior or posterior vaginal wall by such a maneuver. Furthermore, the vaginal manipulator device does not limit the insertion depth into the vagina, nor does it facilitate proper tensioning of these tissues, oftentimes subjecting the vaginal walls and tissues to injury or breakage during the performance of the procedure due to this deficiency, which exposes the patient to markedly increased risk for infection, mesh exposure, poor wound healing and the need for future additional surgical procedures.

BRIEF SUMMARY OF THE INVENTION

One advantage of an embodiment of the invention is for a vaginal manipulator probe apparatus to facilitate surgical repair of the prolapsed vagina, cervix, uterus and pelvic floor without removal for repositioning.

Another advantage of an embodiment of the invention is for the vaginal manipulator probe apparatus to improve safety and efficiency during surgical repair of pelvic prolapse.

Another advantage of an embodiment of the invention is for the device to improve graft placement during surgical repair of pelvic prolapse.

A further advantage of an embodiment of the invention is for the device to facilitate suturing of repositioned tissues during surgical repair.

Yet another advantage of an embodiment of the invention is for the device to facilitate achieving the proper tension of the repositioned organs during surgical repair of prolapse, preventing damage and improving outcomes.

Still yet another advantage of an embodiment of the invention is for the device to facilitate cervical repositioning to shorten excess vaginal length without device removal during surgical repair of prolapse, decreasing the need for additional procedures.

Another advantage of an embodiment of the invention is for the device to facilitate laparoscopic surgical repair of prolapse by inhibiting the escape of abdominal insufflation gas via the vagina.

Other objects and advantages of the present embodiments of the invention will become apparent from the following descriptions, taken in connection with the accompanying drawings, wherein, by way of illustration and example, an embodiment is disclosed.

In accordance with one embodiment, there is disclosed an apparatus for repositioning the vagina, cervix, uterus and pelvic floor and method for securing same comprising: A vaginal manipulator probe with a curved body which facilitates surgical visibility, dissection, and graft placement, a device to elevate, support, and expose the pelvic floor and perineal body during surgical repair, a device to set the proper vaginal insertion depth, a device to properly tension the repositioned tissue, a device to shorten the vaginal wall thereby decreasing the need for additional procedures, a device to substantially inhibit escape of insufflation gas via the vagina during laparoscopy, a method to elevate, support, and expose the pelvic floor and perineal body during surgical repair, a method to set the proper vaginal insertion depth, a method to properly tension the repositioned tissue, a method to shorten the anterior or posterior vaginal wall thereby decreasing the need for additional procedures, and a method to substantially inhibit escape of abdominal insufflation gas via the vagina during laparoscopy.

In accordance with an embodiment of the invention, there is disclosed a process for using an apparatus for repositioning the vagina, cervix, uterus and pelvic floor and a method for securing same comprising the steps of: A vaginal manipulator probe with a curved body along its long axis, configured to be inserted into a vagina, which facilitates surgical visibility, dissection, and graft placement, a device to elevate, support, and expose the pelvic floor and perineal body during surgical repair, a device to set the proper vaginal insertion depth, a device to properly tension the repositioned tissue, a device to shorten the vaginal wall thereby decreasing the need for additional procedures, a device to substantially inhibit escape of abdominal insufflation gas via the vagina during laparoscopy, a method to elevate, support, and expose the pelvic floor and perineal body during surgical repair, a method to set the proper vaginal insertion depth, a method to properly tension the repositioned tissue, a method to shorten the anterior or posterior vaginal wall thereby decreasing the need for additional procedures, and a method to substantially inhibit escape of insufflation gas via the vagina during laparoscopy.

BRIEF DESCRIPTION OF THE DRAWINGS

The drawings constitute a part of this specification and include exemplary embodiments, which may be embodied in various forms. It is to be understood that in some instances various aspects of embodiments may be shown exaggerated or enlarged to facilitate an understanding of those embodiments.

FIG. 2b is an exploded cross sectional view of one element of an embodiment;

FIG. 9 is a diagrammatic view of an alternate element of an embodiment;

FIG. 13 is a view diagrammatic sectional demonstrating the method of use of one element of an embodiment;

DETAILED DESCRIPTION OF EMBODIMENTS

Detailed descriptions of an embodiment are provided herein. While these embodiments are presently contemplated, other embodiment values, dimensions, materials, and shapes can be used. It is to be understood that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

DETAILED DESCRIPTION

Figure 1:
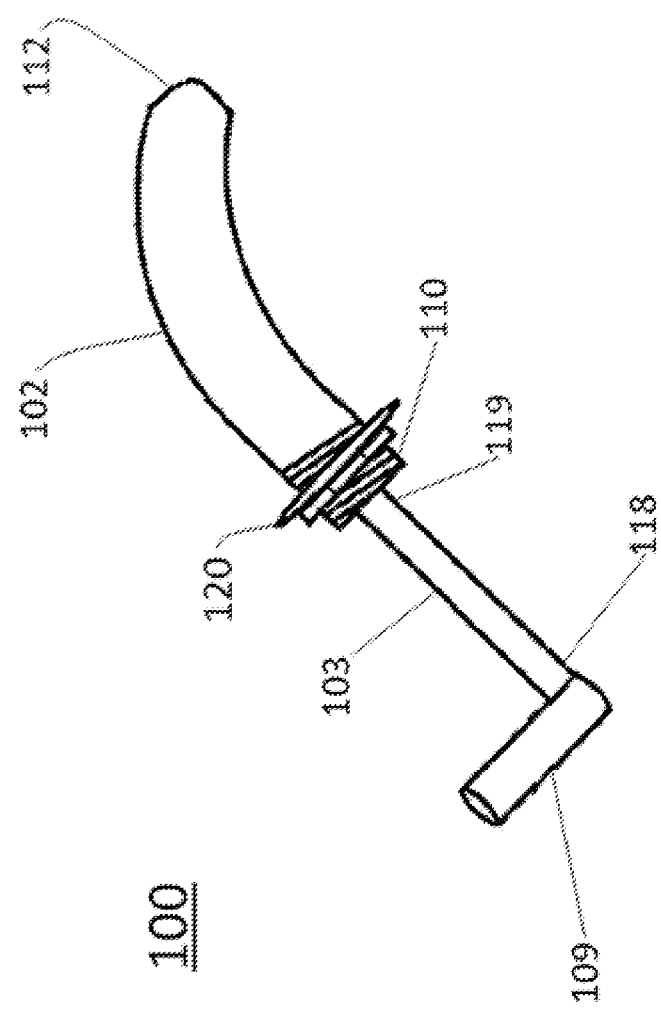
FIG. 1 is a diagrammatic perspective view of one embodiment showing its general arrangements and construction.

FIG. 1 illustrates a vaginal manipulator probe apparatus 100 comprising a vaginal manipulator probe 102 and proximal threaded portion 110 with adjustable disc 120 and external handle 103. The vaginal manipulator probe 102 is configured to be inserted into a vagina 350 (FIG. 3) and is pivotable. The vaginal manipulator body has a substantially solid adjustable disc 120 attached via the threaded cylinder on the proximal portion 110 handle insertion. The vaginal manipulator probe 102 can be configured to receive a cervix and is pivotable. The handle grasp 109 is used to manipulate the machine during a procedure.

Figure 2:
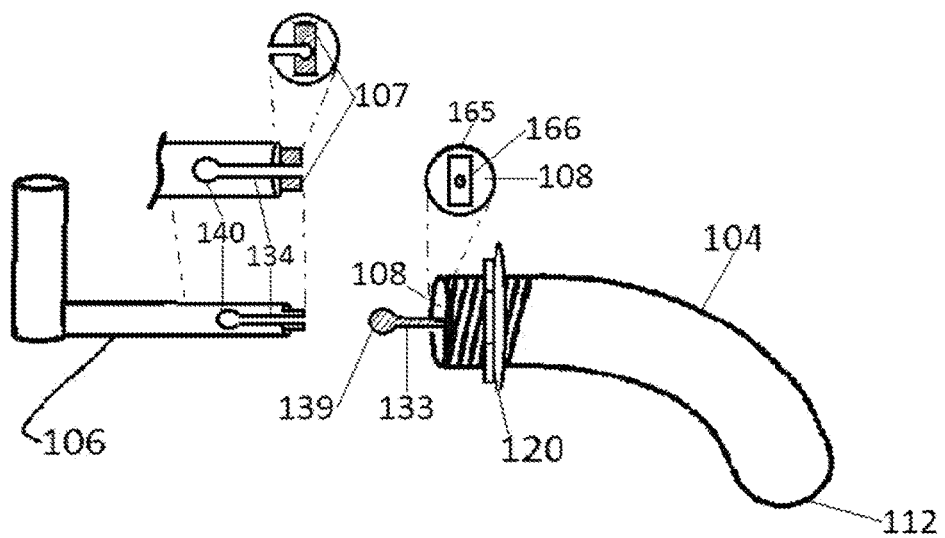
FIG. 2 is an exploded perspective view of one element of an embodiment.

FIG. 2 illustrates a vaginal manipulator probe apparatus comprising a vaginal manipulator probe body 104 in a detached state from the elongate handle shaft 106. A handle 106 can be configured to reversibly receive the probe body 104 to or from the elongate handle shaft 106 by engaging the stem-ball 133 device into the keyhole recess 134 located on the distal portion of the elongate shaft 106, also noted in the exploded view demonstrated in FIG. 2b. The rectangular prominence 107 on the distal end of the elongate shaft 106 in the exploded view is configured to fit into the counter-bore recess 165 on the proximal end of the vaginal probe 104 which leads to a rectangular shaped aperture 166, with a size which closely approximates the size of the rectangular prominence 107. The stem-ball finger 133 centered on the probe 104 proximal end surface 108 and extending proximally as a cylindrical rod 133 with attached sphere 139 on its tip, is configured to be reversibly received in the corresponding key-hole type cylindrical recess 134 with an expanded proximal recess 140 of substantially the same size as the sphere 139 which the recess 140 receives, and positioned in the elongate shaft 106 distal portion, and are pivotable in that recess 134 and 140 until the rectangular prominence 107 is received into the counter-bore recess 165 with rectangular-shaped aperture 166, and the handle is then secured to the probe 104. The rod 133 has a length along its longitudinal axis of about 1 cm to about 5 cm (e.g., about 3 cm), a diameter of about 1 mm to about 6 mm (e.g., about 2 mm), and with a sphere 139 attached on its proximal end with diameter of about 2 mm to about 15 mm (e.g., about 5 mm). The rod 133 can be formed of any of various relatively rigid materials, including metals and polymers. The counter-bore recess 165 and rectangular aperture 166 can be formed by molding (extruding, blow molding or injection molding) and made of medical grade plastics and/or rubber, e.g. natural or synthetic rubber (e.g., silicone) due to their ease of manufacturing, flexibility, availability, and disposable qualities.

Figure 2A:
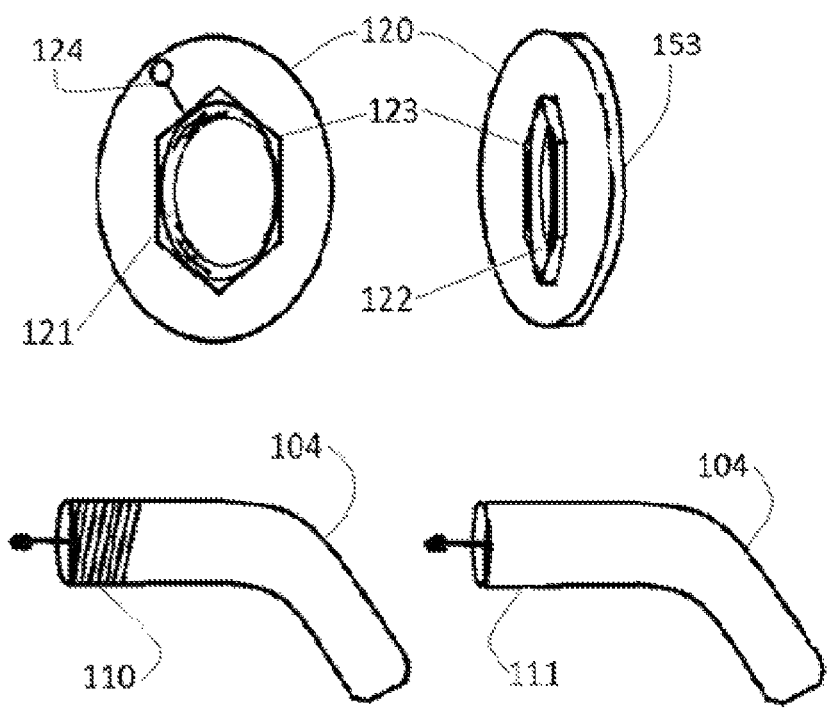
FIG. 2a is a perspective view of one element of an embodiment.

As illustrated in FIG. 2a, the adjustable disc 120 can be configured with either a threaded bore 121 or a smooth bore 122, to correspond to the configuration of the vaginal manipulator probe 104 proximal portion as either threaded 110 or smooth 111, respectively. The adjustable disc 120 can be further configured with a "patient" smooth side 153, and hexagonal adjustment side 123 opposite the smooth side, with or without a thumb set-screw 124.

Figure 2C:
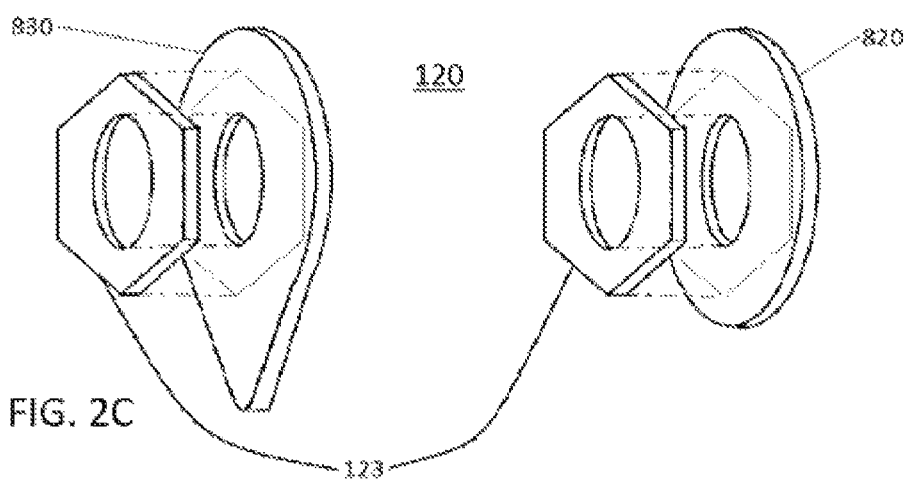
FIG. 2c is a diagrammatic perspective view of one element of an embodiment.

As illustrated in FIG. 2c, the adjustable disc 120 apparatus, although typically circular 820, can be configured in different shapes, such as oval or inverted teardrop 830, and can have a proximal portion 123 with a hexagonal circumference which pivots independently from the distal portion (e.g., inverted teardrop shape 830, circular shape 820), such that the proximal portion 123 can rotate about the axis of the central threaded or smooth bore.

Figure 2D:
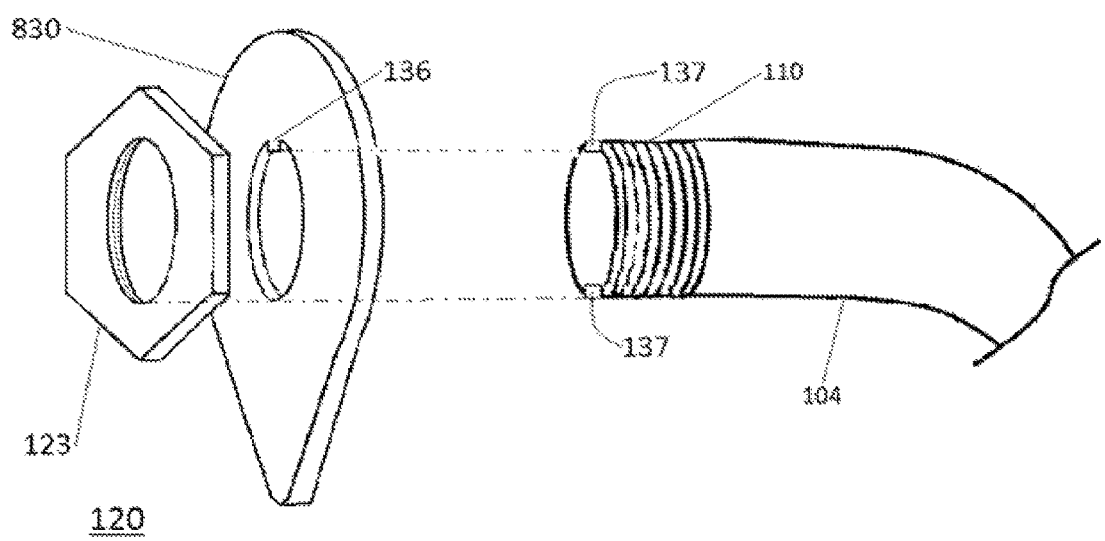
FIG. 2d is an enlarged perspective view of one element of an embodiment.

As illustrated in FIG. 2d, the distal portion of the adjustable disc 120 apparatus can be configured with a key 136, typically a rectangular prominence at the 12 o'clock position extending into the circular bored threaded or smooth recess to a depth of about 1 mm to about 10 mm (e.g., about 3 mm, about 5 mm) with a width of about 3 mm to about 10 mm (e.g., about 2.5 mm, about 6 mm). The key 136 is configured to be received into a corresponding slotted recess 137 on the proximal portion of the vaginal probe manipulator 110. The key 136 facilitates positioning of the oval or teardrop-shaped adjustable disc such that the long axis of the vaginal probe manipulator corresponds to the mid-sagittal plane of the patient in which the vaginal probe manipulator apparatus is disposed.

As will be described below, and illustrated in FIGS. 3-5, 10a-10e, 14, and 16, the vaginal manipulator probe 100 apparatus as illustrated above can be used to reposition any necessary combination of a prolapsed vagina 350, uterus 354 if present and/or cervix 351 if present, and perineal body 348, to assist the surgeon in exposing the rectovaginal space 347 between the vagina 350 and rectum 346, and exposing the vesicovaginal space 345 between the vagina 350 and the bladder 344. The vaginal manipulator probe 100 apparatus can further be used to achieve a uniform depth of insertion, a uniform tension on the tissues to be repositioned, to facilitate the surgeon's effort to expose the tissue planes for surgical dissection, to provide a backstop support for those tissues, thereby facilitating the placement of sutures by the surgeon, and to provide a substantially fluid-tight seal with the tissues and thereby aid the visualization of the pelvic structures during laparoscopy, and the steps by which these implementations can thereby be accomplished will be described.

Figure 3:
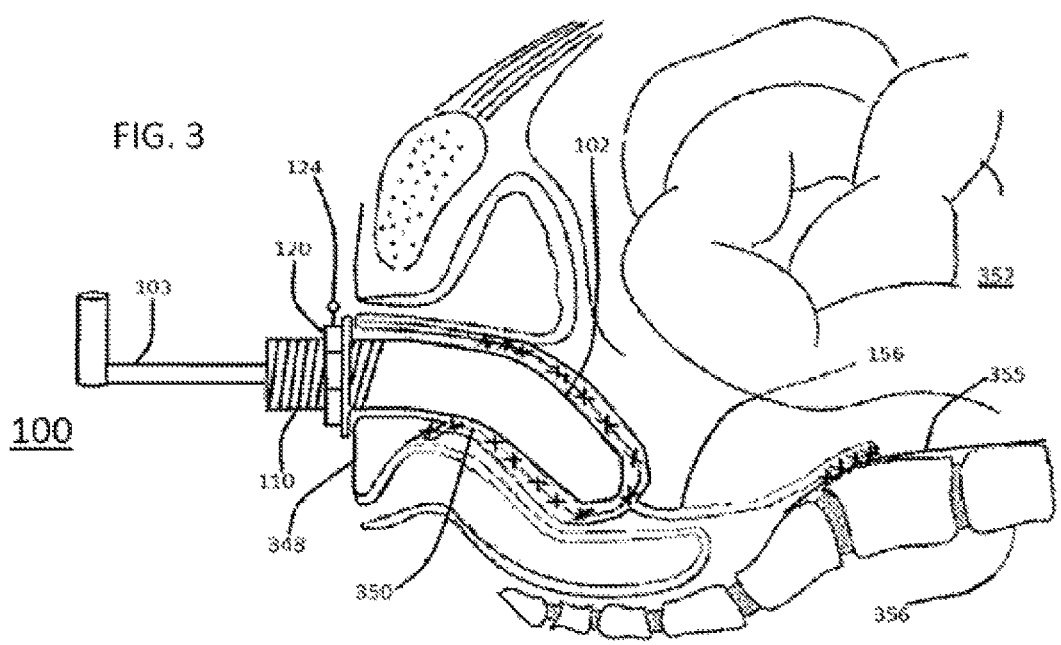
FIG. 3 is a perspective sectional view of an element of an embodiment positioned inside a patient.

One embodiment can be used to reposition the prolapsed vagina during vaginal prolapse correction procedures. As illustrated in FIG. 3, to reposition the vagina 350, the user grasps the handle 103 and inserts the vaginal probe 102 manipulator apparatus into the vagina 350 to the desired depth of insertion as determined by the surgeon. The adjustable disc 120 is then positioned on the threaded proximal portion 110 by rotating the threaded bore of the adjustable disc 120 onto the threads of the vaginal probe 102 until adjacent to the perineal body 348, then tightening the thumb screw 124, thereby inhibiting any further depth of insertion. By moving the handle 103, the vaginal manipulator probe 102, the perineal body 348 with associated pelvic floor, and the vagina 350 in which the probe 102 is disposed, can also be moved. The vaginal manipulator probe is a largely cylindrical or oval shaft curved along its long axis to conform to the natural vaginal curvature, with attached adjustable disc 120 which can be used to reposition vaginal prolapse during prolapse repair procedures or pelvic reconstructive surgery. With the probe 102 apparatus disposed in the vagina 350, the adjustable disc 120 can be adjusted to be adjacent to the perineal body 348 and will substantially inhibit the escape of insufflation gas from the abdomen 352 via the vagina 350 during a laparoscopic procedure.

Figure 4:
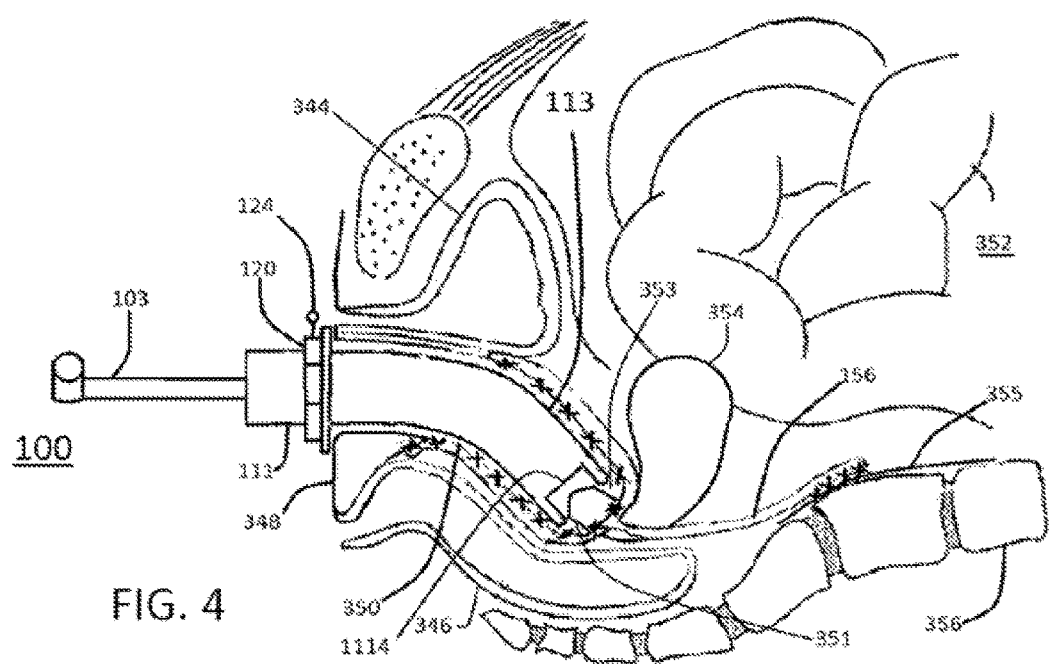
FIG. 4 is a perspective sectional view of an embodiment with tip variation inside a patient.

As illustrated in FIG. 4, the vaginal manipulator probe body 113 is a largely cylindrical or oval shaft curved along its long axis, which can be configured with a distal slotted recess 1114, and with attached adjustable disc 120, can be used to reposition the prolapsed uterus 354 and vagina 350 during prolapse repair procedures. The distal slotted recess 1114 is configured to reversibly receive the uterine cervix 351. Rotation of the handle 103 by the user can be performed during the repair procedure to optimize the position of the vagina 350 and cervix 351 or uterus 354, without being hindered by the presence of the cervix 351 or uterus 354. With the probe apparatus 113 disposed in the vagina 350 and distal slotted recess 1114 receiving the uterine cervix 351, the adjustable disc 120 can be adjusted to be adjacent to the perineal body 348 and will substantially inhibit the escape of insufflation gas from the abdomen 352 via the vagina 350 during laparoscopy.

Figure 5:
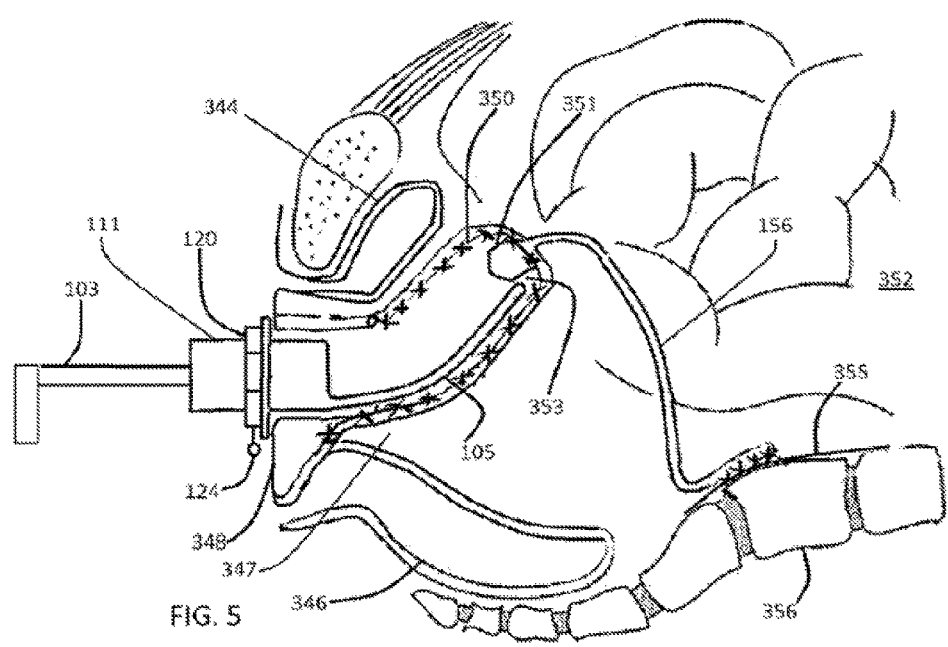
FIG. 5 is a diagrammatic perspective sectional view demonstrating an aspect of operation of an embodiment.

Referring to FIG. 5, one embodiment of the probe device can be configured with a single curved blade distal tip 105 which may be used to reposition the prolapsed uterine cervix 351 and vagina 350 during uterovaginal or cervicovaginal prolapse correction procedures. As illustrated in FIG. 5, to reposition the perineal body 348, and/or the uterine cervix 351 and vagina 350, the user grasps the handle 103 with attached bladed probe 105 and inserts the vaginal probe 105 manipulator assembly into the vagina 350 to the desired depth of insertion as determined by the surgeon. In some embodiments of the invention, the adjustable disc 120 is then positioned on the smooth proximal portion 111 by sliding the smooth bore of the adjustable disc 120 onto the smooth proximal portion of the vaginal probe 105 until adjacent to the perineal body 348, then tightening the thumb set-screw 124, thereby inhibiting any further depth of insertion. The bladed probe tip 105 is configured to be positioned adjacent to the cervix 351 in the vaginal fornix 353. By moving the handle 103, the vaginal manipulator probe 105 and the vagina 350 in which the probe 105 assembly is disposed, and uterine cervix 351 can also be moved, assisting the surgeon's effort to expose the surgical spaces between the vagina and rectum, and between the vagina and bladder, and to expose the desired tissue surfaces to be sutured during a pelvic reconstructive procedure, such as sacrocolpopexy.

One embodiment of the device may be used to reposition the prolapsed perineal body during pelvic reconstruction procedures. As illustrated in FIG. 3, to reposition the perineal body 348, the user grasps the handle 103 and inserts the vaginal manipulator probe 102 into the vagina 350, advancing the apparatus until the desired depth is achieved. The user positions the adjustable disc 120 adjacent to the perineal body 348 and tightens the thumb set-screw 124. By moving the handle 103, the vaginal manipulator probe 102 and the vagina 350 in which the probe assembly is disposed, and with the adjustable disc 120 positioned adjacent to the perineal body 348, these structures can also be moved. One embodiment of the vaginal manipulator probe body 102 is a largely cylindrical or oval shaft curved about its long axis, with attached adjustable disc 120 which can be used to reposition the perineal body 348 during prolapse repair procedures. With the probe assembly 102 disposed in the vagina 350, the adjustable disc 120 can be adjusted to be adjacent to the perineal body 348 and will substantially inhibit the escape of insufflation gas from the abdomen 352 via the vagina 350 during laparoscopy. With the probe assembly 102 disposed in the vagina 350, the adjustable disc 120 assembly can be adjusted to contact and elevate the perineal body 348 to aid in exposing the rectovaginal space and vesicovaginal space to be dissected, to provide substantially uniform tension on the repositioned tissues, and once those tissues are elevated into the desired position in the pelvis, to aid in the placement of sutures by the surgeon to support these structures in the desired position.

As will be described in greater detail below, one embodiment of the vaginal manipulator probe body 102 is coupled to an elongate shaft with handle 103, as in FIG. 1.

As illustrated in FIG. 1, an embodiment of the vaginal manipulator probe body 102 couples to an elongate shaft with handle 103 having a proximal end portion 118 and a distal end portion 119. A grip handle 109 is coupled to the proximal end portion 118 of the shaft 103. The handle 109 can be formed integrally with the shaft 103 or can be formed as a separate entity and attached to the shaft 103. The distal end 119 of the shaft is configured to securely attach to the vaginal manipulator probe. In certain embodiments of the invention, the vaginal manipulator probe is formed integrally with the shaft 103.

Figure 6:
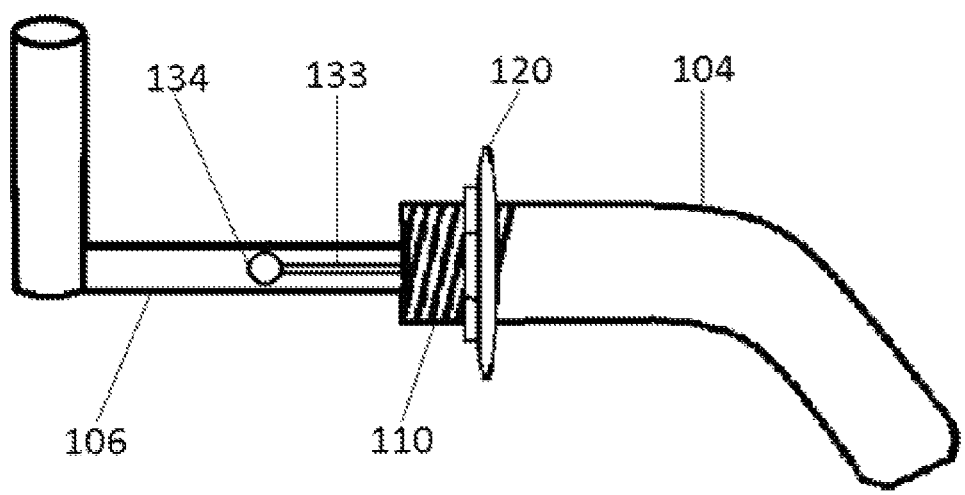
FIG. 6 is a perspective view of an assembled variation of an embodiment.
Figure 7:
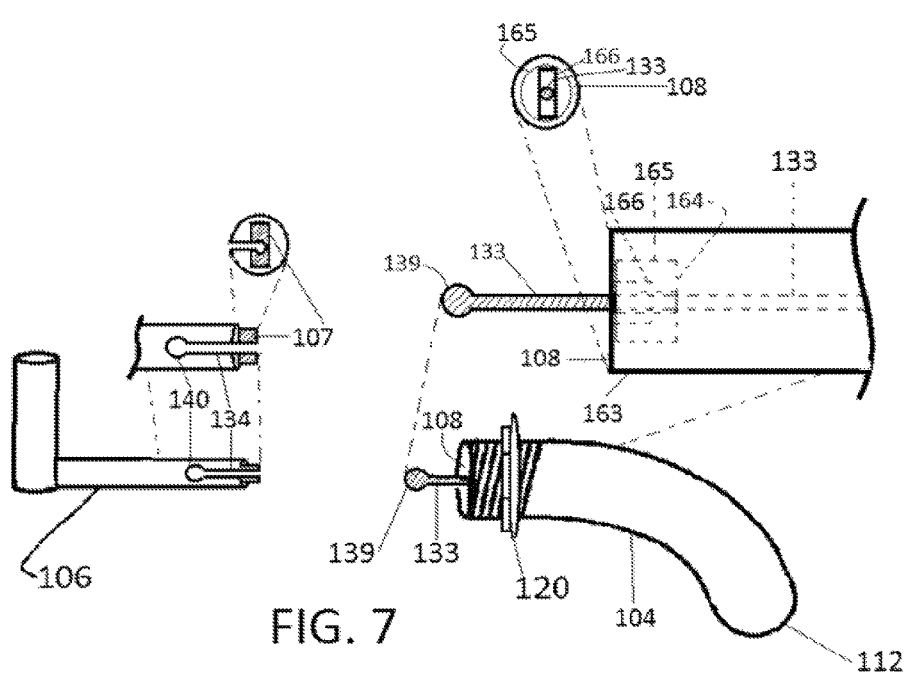
FIG. 7 is a diagrammatic exploded view of disassembled embodiment of FIG. 6.

FIGS. 6 and 7 illustrate an embodiment of the vaginal manipulator probe apparatus 104 with the vaginal manipulator elongate shaft handle 106, in the attached and detached state, respectively. Referring first to FIG. 6 illustrates the handle 106 securely attached to the vaginal manipulator probe apparatus 104. In certain configurations, as illustrated in FIG. 7, the handle 106 can be detached from the probe 104. In the detached state, the user is able to reattach the handle 106 to the probe at a different rotational angle (e.g., 0 degrees, 180 degrees) corresponding to the rectangular-shaped prominence 107 which extends out from the distal end of the handle 106, and closely resembles the size and shape of the proximal surface 108 of the proximal end 163 of the vaginal probe 104 which is configured to receive it through the rectangular aperture 166 into the counter bore recess 165. A centrally positioned male stem with ball 133 configuration is utilized to be reversibly received by the recess 134 of the distal portion of the handle 106 such that the two different rotational positions are possible if desired by the user. After the handle is attached, or prior to attachment, the adjustable disc 120 is threaded onto the probe 104 assembly to the user-defined depth. Referring to FIG. 5, the adjustable disc 120 can facilitate control of the insertion depth of the vaginal probe manipulator apparatus 105 into a vagina 350, and with the use of the thumb set-screw 124 to secure the adjustable disc 120 in the desired position, inhibit further undesired movement of the probe into the vagina 350. For similar reasons, the forces placed on the pelvic floor, vagina 350, and uterine cervix 351 will be more uniform, as these forces are more evenly dispersed throughout the points of contact made by the adjustable disc 120 on the perineal body 348 and the probe 105 on the vaginal walls. The surgeon may also adjust the disc 120 to support proportionately more force on the perineal body rather than the weaker vaginal walls, decreasing the risk of vaginal wall injury which could result from excessive force or pressure when the user pushes the entire apparatus into the pelvis during a procedure.

Figure 7A:
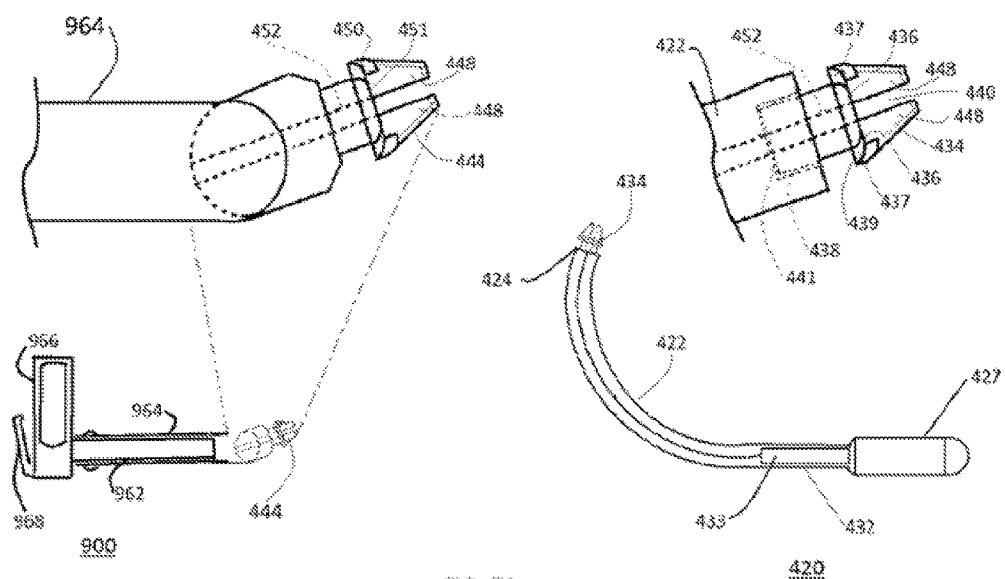
FIGS. 7a-7b is a diagrammatic exploded view of variations and detail of one element of an embodiment.

In another embodiment of the vaginal manipulator probe apparatus, a handle assembly 900 shown in FIG. 7a is for securing the vaginal probe manipulator 104 shown in FIG. 7. One type of handle 900 is illustrated in FIG. 7a, with a tip hub 444 which is configured to releasably receive and support the manipulator probe 104 illustrated in FIG. 7. In this regard, the tip hub 444 includes a pair of spaced apart flats 448 which extend upwardly from a first surface 451 of a hub base 450. The tip hub 444 can be inserted into the counter-bore hole 165 illustrated in FIG. 7b in the tip base 163 and into a position in which the spaced apart flats 448 engage the rectangular aperture 166 as in FIG. 7b. Referring again to FIG. 7a, the tip hub 444 also includes a central recess 452 for receiving the proximal portion of the rod 160a shown in FIG. 7b. As discussed below, the counter-bore hole 165 (FIG. 7b) and the rectangular aperture 166 allow the probe 104 (FIG. 7) to be securely mounted to the handle 900 (FIG. 7a). A suitable manipulator handle is commercially available from CooperSurgical, Trumbull, Conn., under the name RUMI® handle.

As further illustrated in FIG. 7a, an elongate curved shaft with proximal handle with adjacent mounting interface is available as an assembly 420. The mounting interface 432 includes a pair of diametrically opposed flat regions 433 formed on the shaft 422. The mounting interface 432 is configured to allow the shaft 422 to be mounted to an adapter of an apparatus for positioning and holding in place a manually manipulated medical device during performance of a robotically assisted medical procedure, such as described in U.S. patent application Ser. No. 11/847,154, filed Aug. 29, 2007, the complete disclosure of which is incorporated herein by reference.

A probe 104 illustrated in FIG. 7 can be releasably secured to a handle apparatus for positioning and holding a manually manipulated medical device during performance of uterovaginal prolapse repair procedures, such as described in U.S. patent publication 2010/0106163, published Apr. 29, 2010, the complete disclosure of which is incorporated herein by reference. With further reference to FIG. 7a, the manipulator 420 also includes a tip hub 434 disposed at the distal end portion 424. The tip hub 434 is configured to releasably receive and support the probe 104 in FIG. 7. The tip hub 434 includes a pair of spaced apart flats 448 which extend upwardly from a first surface 436 of a base 437. A stem 438 extends from a second surface 439, opposite the first surface 436 of the base 437. A through hole 440 extends from the first surface 436 of the base 437 through the stem 438 and is sized to receive a rod 159 (FIG. 7b) of the probe 104 shown in FIG. 7. The stem 438 is received in an aperture 441 in the shaft 422 in a press-fit manner, thereby securing the tip hub 434 to the shaft 422. A suitable manipulator handle is commercially available from CooperSurgical (Trumbull, Conn.), under the name RUMI Arch™.

Figure 7B:
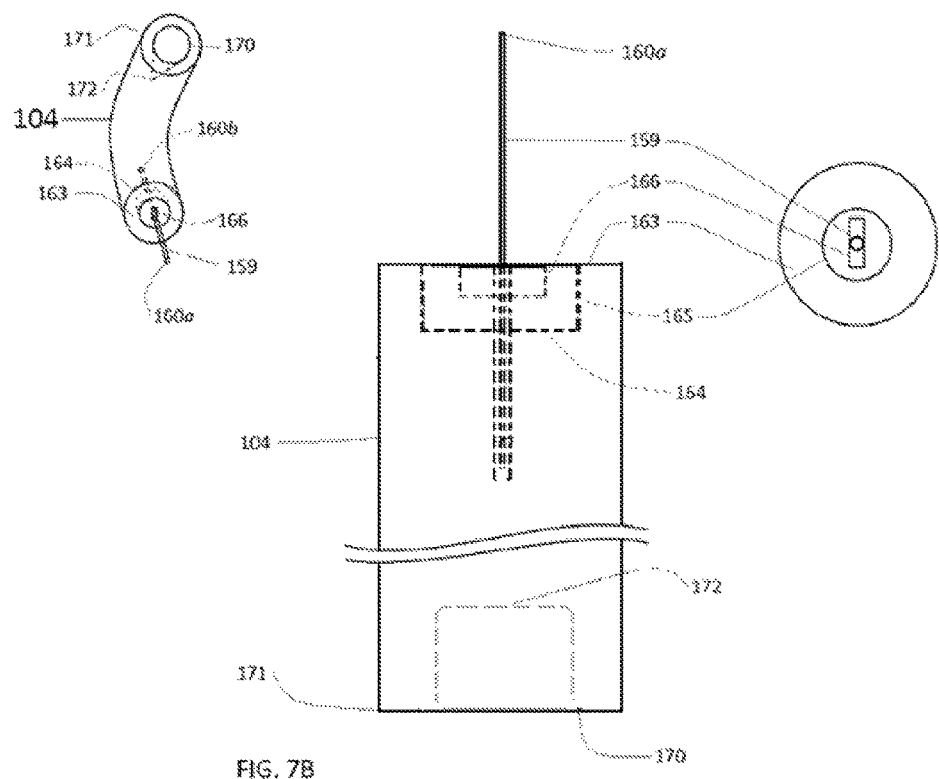

In another embodiment, as illustrated in FIG. 7B, the probe tip 104 is configured to receive a cervix at the distal end surface 171 with central circular recess 170 extending to more proximal surface 172. The largely cylindrical recess is configured to receive a uterine cervix, and is a diameter of about 1 cm to about 5 cm (e.g., about 3 cm, about 4 cm) extending to a depth of about 1 cm to about 4 cm (e.g. about 2 cm, about 3 cm) to approximate the size of the patient's cervix to be received in this recess.

The elongate shafts, handles, and manipulator probe assemblies discussed above can be formed, e.g. molded and/or machined, from materials that are biocompatible and capable of withstanding heat-based medical sterilization procedures (e.g., autoclave, steam autoclave, or dry heat oven) so that the vaginal manipulator probe assemblies can be sterilized and re-used after a treatment. Suitable materials that are capable of withstanding medical device sterilization procedures include metals, such as stainless steel and aluminum, and polymers, such as polyoxymethylene (POM) commonly known under the DuPont™ brand name Delrin®.

Figure 8:
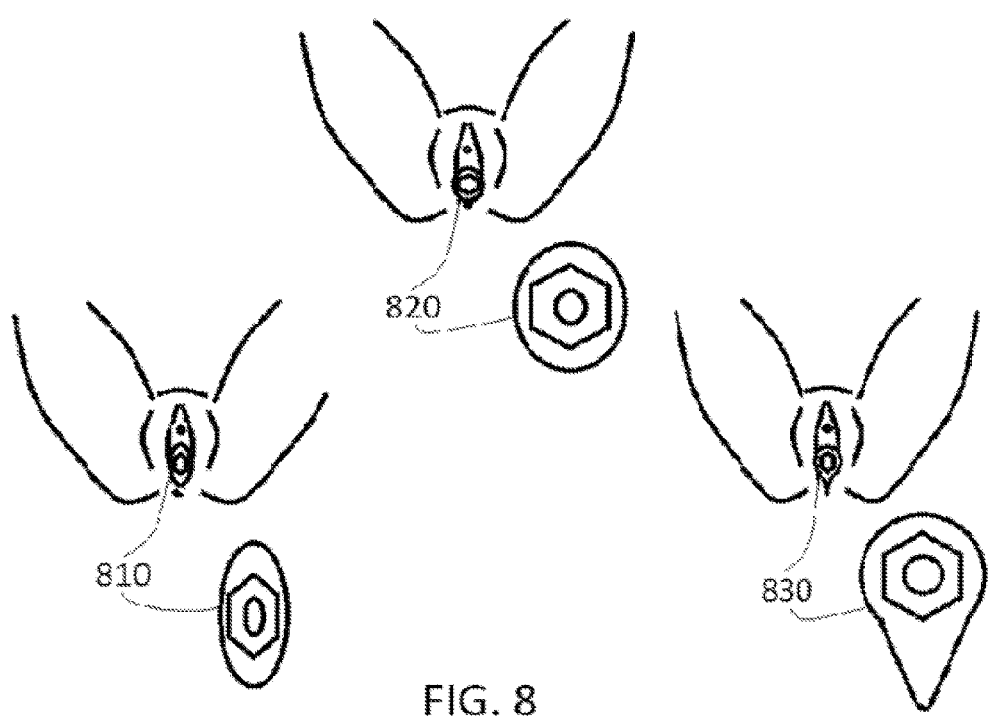
FIG. 8 is a perspective view of variations of one element of an embodiment.

As illustrated in FIG. 2a, in one embodiment the distal (patient side) surface of the adjustable disc 120 forms a smooth, flat, low-friction surface. The disc 120 is washer-shaped with a central circular opening with threads 121 cut into the bore to match the threads on the vaginal manipulator probe body 110 as depicted in FIG. 6. The disc 120 can be from 0.5 cm larger than the diameter of the vaginal probe 104, up to 5 cm larger than the diameter of the vaginal probe 104. In some implementations, the adjustable disc 120 is circular, as 820 in FIG. 8. Also referring to FIG. 8, in other implementations, the adjustable disc 120 is an oval 810 or inverted teardrop 830 shape, to conform to variations in patient anatomy. In some configurations, as illustrated in FIG. 2c, the central hexagonal portion 123 can rotate independently from the larger circular disc portion, which facilitates threaded adjustment onto the threaded probe body proximal end, without the need to reposition or rotate the larger disc portion, for which positioning as in FIG. 8 of the oval 810 and inverted teardrop 830 shapes against the narrow area between the upper thighs and buttocks is facilitated by sliding it over the probe 104 as shown in FIG. 2B shaft without rotation. The disc 120 shown in FIG. 2C and the discs 810, 820, and 830 in FIG. 8 may be molded and/or machined of metals, such as stainless steel and aluminum, and polymers, such as polyoxymethylene (POM) commonly known under the DuPont™ brand name Delrin®, polyoxymethylene, or other biocompatible rigid thermoplastic or thermoset materials such as polycarbonate (Lexan®) and acrylonitrile butadiene styrene (ABS). Other examples of suitable materials include nylon, silicone, polyethylene, or polyvinyl chloride.

In certain implementations, the adjustable disc 120, as shown in FIG. 2a with the vaginal manipulator probe 104, has a proximal side typically positioned opposite from the perineum, and an opposite distal flat side configured to be positioned adjacent to the perineum, and a central threaded bore 121 which corresponds to the proximal threaded portion 110 of the vaginal manipulator probe 104. The proximal side of the adjustable disc 120 as shown in FIG. 2a has a centered, hexagonal circumference 123 configuration extending proximally from the flat portion about 2 mm to about 30 mm (e.g., about 4 mm, about 10 mm), and having a diameter about 0.5 cm to about 3 cm (e.g., about 3 cm, about 1.5 cm) less than the maximum disc diameter. In certain configurations a thumb set-screw 124 is located on a flat portion of the hexagon 123 to secure the adjustable disc 120 after positioning by the user. This can help the surgeon to adjust and secure the position of the disc 120 on the vaginal manipulator probe 104 by hand without additional tools, to substantially inhibit the leakage of gas from the patient's vagina, support and elevate the perineal body, and facilitate placement of the vaginal manipulator probe 104 to the proper vaginal insertion depth, with the proper degree of tension on the tissues.

In some implementations, the adjustable disc as shown in FIG. 2a has a smooth inside bore 122, and has a proximal side 123 with a circumferentially positioned series of connected flat surfaces in the shape of a hexagon, much like the head of a hexagonal bolt, extending proximally out from the larger adjustable disc surface for about 2 mm to about 30 mm (e.g., about 10 mm) and typically positioned opposite from the perineum, and a distal smooth flat side 153 configured to be positioned adjacent to the perineum. The width of the flat areas typically are of a size to accommodate a surgeon's fingers, to assist the surgeon with sliding the adjustable disc 120 in a pushing movement onto the proximal probe smooth portion 111, without the use of additional tools, until the desired position is obtained and the disc 120 can thereby be secured in place with the thumb set-screw 124 illustrated in FIG. 2a.

As illustrated in FIG. 3, certain embodiments of the vaginal manipulator probe 102 have a length that is at least 0.5 times (e.g., 0.75 times, 1.0 times) the length of the vagina 350 in which it is to be disposed. In some implementations, the vaginal manipulator body has a length of about 5 cm to about 18 cm (e.g., about 8 cm to about 12 cm, about 13 cm). In some implementations, the vaginal manipulator probe 102 has a diameter that approximately matches the diameter of the vagina 350 in which it is to be inserted. In certain implementations, the vaginal manipulator probe 102 has a diameter of about 3 cm to about 6 cm (e.g., about 4 cm to about 5 cm, about 5 cm) with a proximal cylindrical threaded portion extending longitudinally for about 3 cm to about 8 cm (e.g., about 4 to about 6 cm, about 5 cm), the threaded portion 110 of the vaginal manipulator probe 102 to receive the threaded portion of the adjustable disc 120. The vaginal manipulator probe 102 has a distal rounded tip which generally conforms to the top region of the vagina 350. The rounded end region extends proximally about 1 cm to about 3 cm (e.g., about 2 cm) from the distal end of the vaginal manipulator probe 102.

In certain implementations, as illustrated in FIG. 5, the vaginal manipulator probe 105 approximates a flattened oval cross sectional shape and the width of the widest portion approximately matches the diameter of the vagina 350 in which it is to be inserted. In certain implementations, the vaginal manipulator probe 105 has a width of about 3 cm to about 6 cm (e.g., about 4 cm to about 5 cm, about 5 cm), with a proximal cylindrical smooth portion extending longitudinally for about 3 cm to about 8 cm (e.g., about 4 to about 6 cm, about 5 cm), the smooth portion of the vaginal manipulator probe 105 closely matches with the smooth bore portion of the adjustable disc 120. The vaginal manipulator probe flattened oval body 105 has a distal rounded tip which generally conforms to the top fornix 353 region of the vagina 350, and is curved about its long axis. The rounded end region extends proximally about 1 cm to about 3 cm (e.g., about 2 cm) from the distal end of the vaginal manipulator probe 105.

Figure 6A:
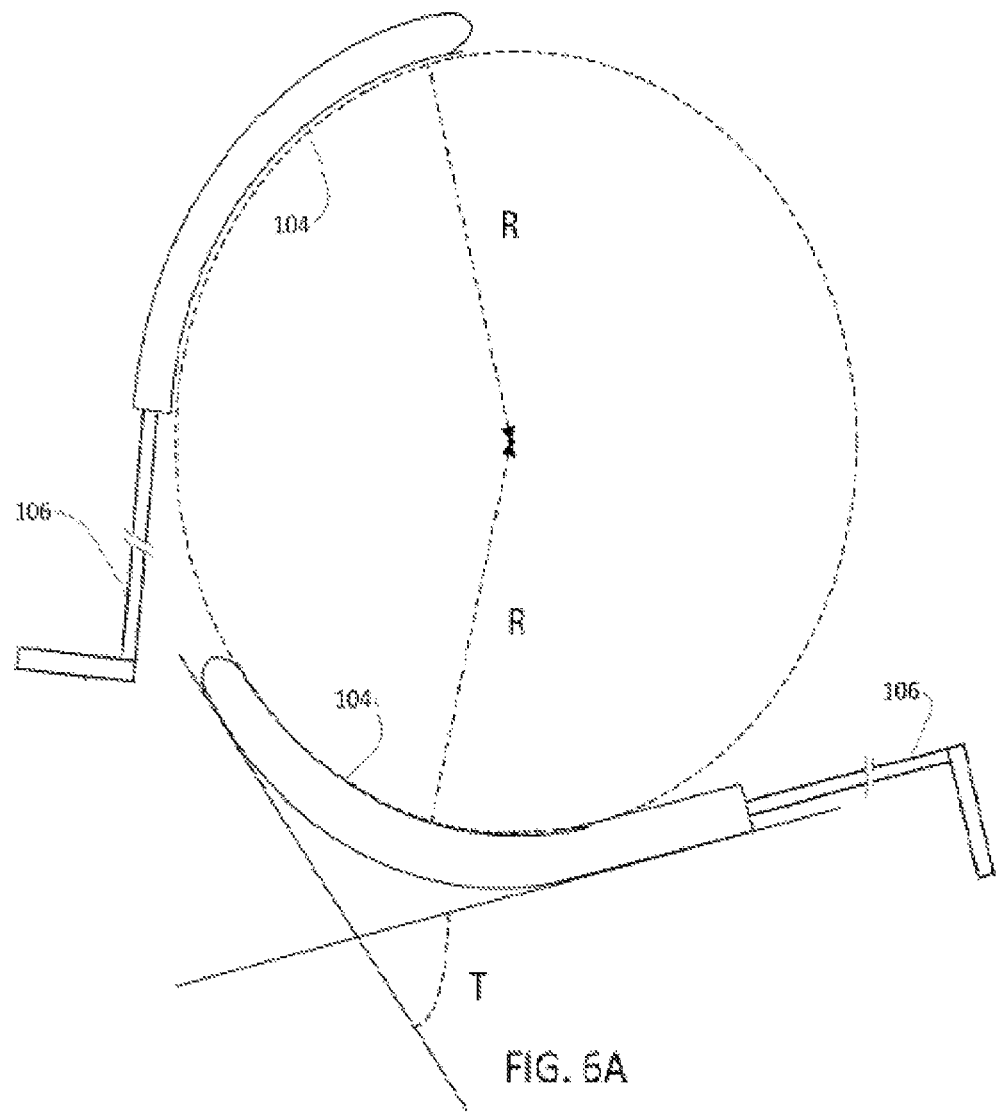
FIG. 6a is a schematic view of one aspect of an embodiment.

As further illustrated in FIG. 6a, the vaginal manipulator probes described above are curved about their long axis in certain embodiments. The arc of the curve is described by a portion of the circumference of a circle with radius (R) of about 5 cm to a radius of about 20 cm (e.g., about 10 cm, about 20 cm) as depicted in FIG. 6a.

In certain other embodiments, as illustrated in FIG. 6a, the vaginal manipulator probes have a substantially straight proximal portion of about 2 cm to about 10 cm in length (e.g., about 5 cm, about 8 cm), and a distal portion which can be curved about its long axis or straight, and is about 2 cm to about 10 cm (e.g., about 4 cm, about 9 cm) in length, and at an angle to the proximal portion whereby a tangential line parallel to the proximal portion along a longitudinal axis describes an angle with a tangential line parallel to the longitudinal axis of the distal portion, the angle (T in FIG. 6a) of which may be formed by the two lines and vary between about 10 degrees in the smallest arc, to about 90 degrees in the largest arc (e.g., about 30 degrees, about 60 degrees). The distal portion may be substantially straight, or curved along its longitudinal axis as described above.

The vaginal manipulator probes described above can be molded and/or machined of metals, such as stainless steel and aluminum, and polymers, such as polyoxymethylene (POM) commonly known under the DuPont™ brandname Delrin®, polyoxymethylene, or other biocompatible rigid thermoplastic or thermoset materials such as polycarbonate (Lexan®) and acrylonitrile butadiene styrene (ABS). Other examples of suitable materials include nylon, silicone, polyethylene, or polyvinyl chloride. Typically the probe embodiments have a color which differs substantially from flesh (e.g., vagina tissue) such that the vaginal manipulator probe provides a distinct color variance when it is positioned adjacent to vaginal tissue. This color variance can assist a surgeon to distinguish the vaginal manipulator probe from the vaginal tissue during surgical procedures.

As illustrated in FIG. 9, in certain embodiments the vaginal manipulator probe 102 can be reversibly received and secured to an elongate shaft and handle 900 through an opening in the proximal end 135 of the vaginal manipulator probe 102. A tip hub on the elongate shaft and handle 900 can contain a tip hub assembly as described above, which can be reversibly received by a counter-bore rectangular aperture 135 and can be inserted into the vaginal manipulator probe 102 proximal end with this tip hub assembly by engaging this aperture 135. Further information regarding suitable mechanism for securing the vaginal manipulator probe 102 to the elongate shaft and handle 900 can be found in US Patent Application Publication No. 2010/0106163, which is incorporated by reference herein.

Figure 10A:
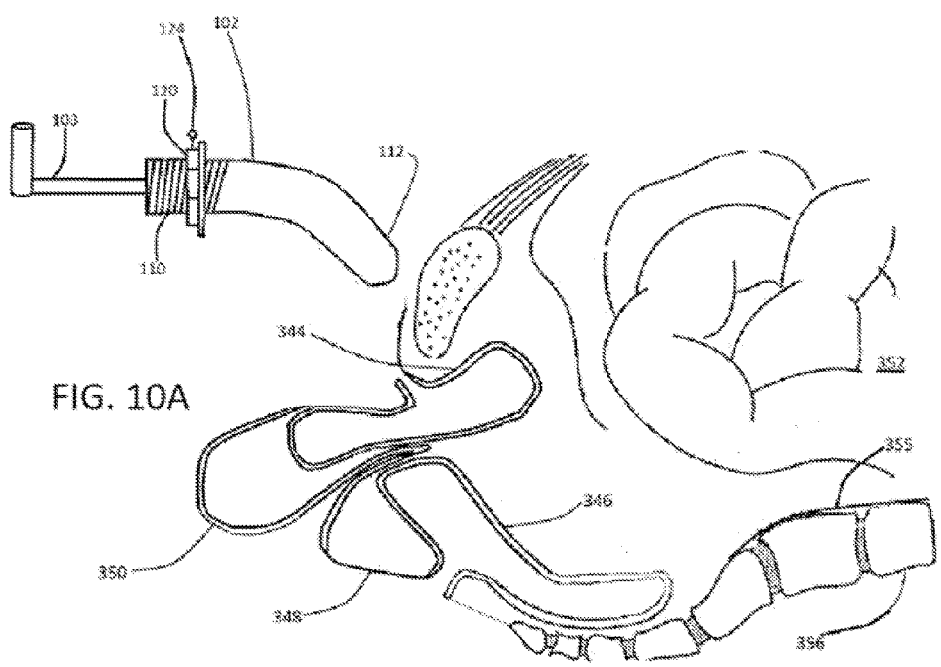
FIGS. 10a-10e are diagrammatic cross sectional sketches showing operation of an embodiment.

FIGS. 10a-10e schematically illustrate steps of a method of using the vaginal manipulator probe 102 to reposition a patient's prolapsed vagina 350 and perineal body 348 during a vaginal prolapse correction procedure, namely a sacrocolpopexy procedure. In this case, the patient previously underwent a total hysterectomy procedure, and as a result, no longer has a uterus or cervix. Referring to FIG. 10a, the surgeon first grasps the elongate shaft and handle 103 and positions the vaginal manipulator probe 102 adjacent to the top portion of the vagina 350 which is located outside of the body as a result of pelvic organ prolapse. The prolapsed vagina 350 is repositioned back into the body to the depth determined by the surgeon. The adjustable disc 120 may then be hand tightened on the threads 110 of the proximal vaginal manipulator probe 102 until contacting the perineal body 348, and the thumb set-screw 124 can be tightened to inhibit further penetration into the vagina 350. The distal rounded end 112 of the vaginal manipulator probe 102 contacts the upper portion of the prolapsed vagina 350.

Figure 10B:
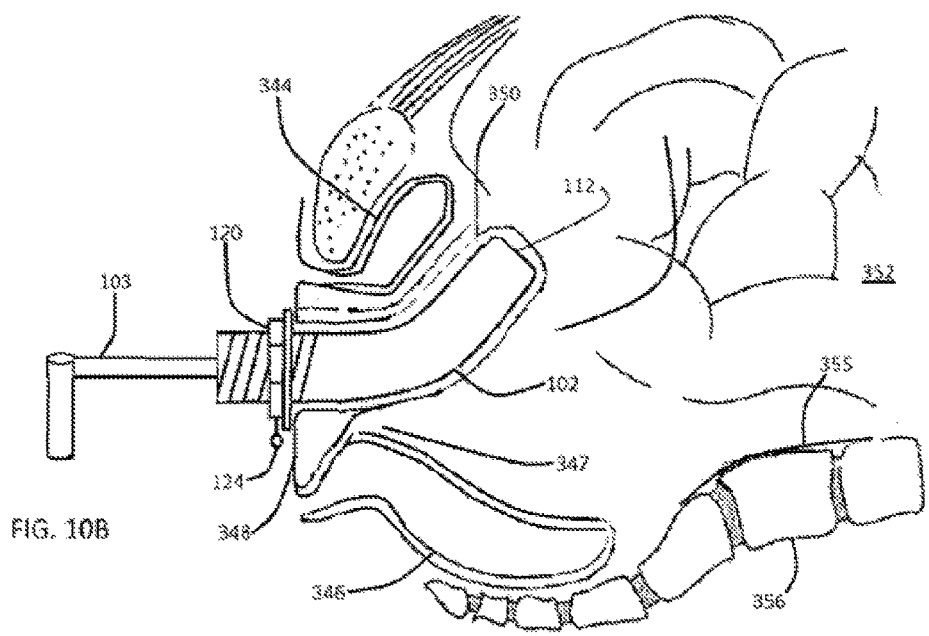

Referring to FIG. 10b, as a result of advancement of the vaginal manipulator probe 102 into the vagina 350, the upper portion of the vagina 350 is eventually contacted by the distal end 112 of the vaginal manipulator probe 102. The adjustable disc 120 is then rotated clockwise on the threaded shaft of the vaginal manipulator probe 102 proximal end until contact is made by the adjustable disc 120 adjacent to the perineal body 348. In some implementations, the surgeon verifies that the proper depth of insertion of the vaginal manipulator probe 102 into the vagina 350 has been achieved and secures the adjustable disc 120 in place by tightening the thumb set-screw 124 through the hexagonal nut surface, against the vaginal manipulator probe threads 110, inhibiting over-penetration into the vagina and providing a substantially fluid-tight seal as described above. The handle 103 is pushed upward into the patient until the vagina 350 and perineal body 348 have been repositioned or raised to the desired location and tension, as shown in FIG. 10b.

Referring to FIG. 10b, prior to or after repositioning the vagina 350 as desired, the abdominal cavity 352 is insufflated with gas (e.g., $CO_2$) and desired surgical instruments, including a laparoscope, are inserted into the abdominal cavity 352 of the patient. The insufflation of the abdominal cavity 352 improves visibility and accessibility to the female pelvic organs for the surgeon.

Prior to placement of sutures in the vagina 350 and perineal body 348, the surgeon can dissect between the rectum 346 and the vagina 350 to open the rectovaginal space 347. The longitudinal curve of the vaginal manipulator probe 102 can be positioned to facilitate this dissection by rotating the handle 103 through 180 degrees as illustrated by FIG. 10b to assist with separation of the vagina 350 from the rectum 346 without additional repositioning movements.

Figure 10C:
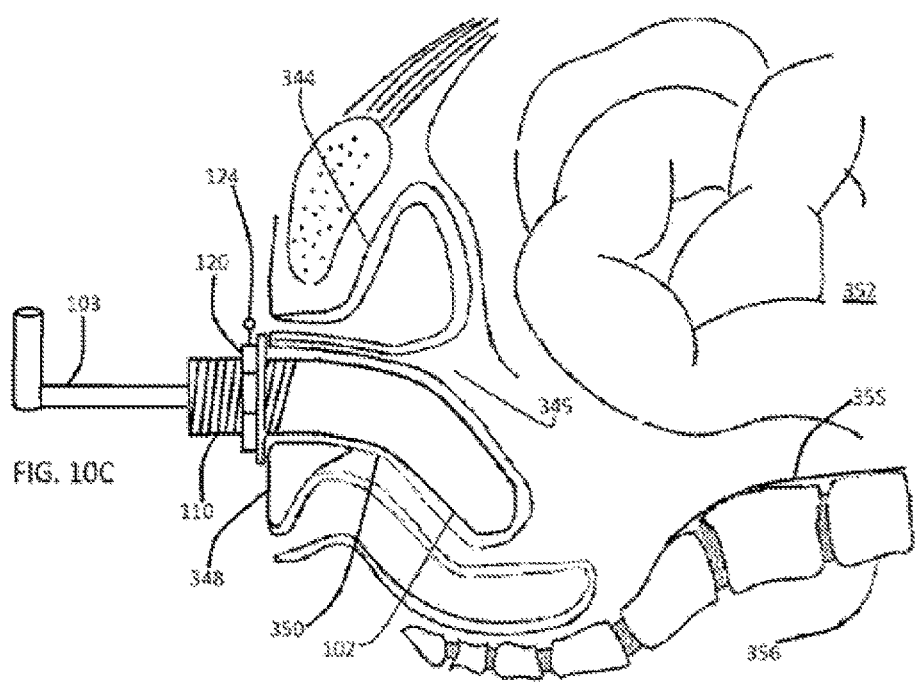

Once the rectovaginal space 347 has been adequately dissected, the internal portion of the perineal body 348 and muscles of the pelvic floor are identified and adequately exposed, the handle 103 is then rotated 180 degrees such that the vaginal manipulator probe 102 and the vagina 350 are positioned posteriorly, and the anterior dissection may be performed by the surgeon in the vesicovaginal space 345, separating the bladder 344 from the vagina 350 as illustrated in FIG. 10c. In this position, the curve of the vaginal manipulator probe 102 facilitates the separation of the vagina 350 and the bladder 344, improving exposure, visibility and accessibility to the vesicovaginal space 345 and serving as an aid to graft placement in this space by the surgeon without additional repositioning movements.

Figure 10D:
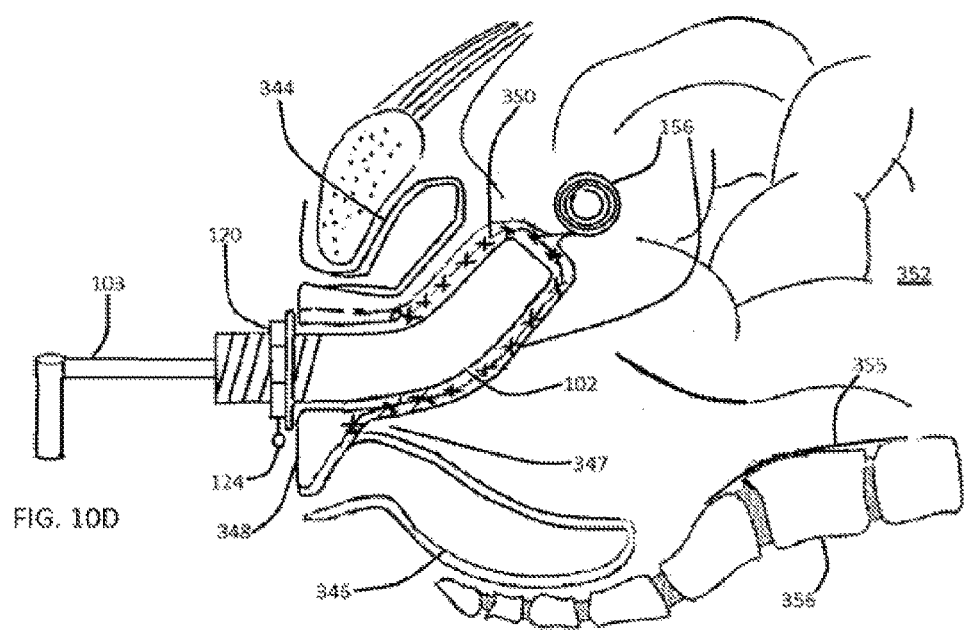

Referring to FIG. 10d, the vagina 350 is secured to the anterior longitudinal ligament 355 overlying the sacral vertebra 356 via a Y-shaped graft 156, which can be made of synthetic material (polypropylene or polyester) or a natural material (e.g., fascia or dermis), by first securing the graft material to the anterior and posterior fascia of the vagina 350 using laparoscopic instruments. While suturing the Y-shaped graft 156 to the vagina 350, the vaginal manipulator probe 102 can help the surgeon to properly position the sutures within the vaginal tissue. The vaginal manipulator probe 102 can be used as a thimble to provide a back-stop to aid in driving the needles and suture material into the vaginal wall. Due to the curved length and depth of insertion of the vaginal manipulator probe 102, a portion of the vaginal manipulator probe 102 is typically adjacent to the vaginal wall being sutured at all locations. As a result, it is not typically necessary to move the manipulator probe 102 during the suturing process of the anterior wall. The vaginal manipulator probe 102 is typically rotated 180 degrees to facilitate the exposure of the posterior vaginal wall with no additional movement necessary for suturing.

The punctures created in the vaginal wall during the placement of sutures may cause the insufflation gas to escape from the abdominal cavity 352 via the vagina 350. However, the adjustable disc 120 substantially inhibits the insufflation gas escaping from the abdomen 352 via the vagina 350 and helps maintain the pneumoperitoneum. Maintenance of the pneumoperitoneum helps to ensure that the visibility within the abdominal cavity 352 of the patient remains adequate for the surgeon to complete the procedure.

Figure 10E:
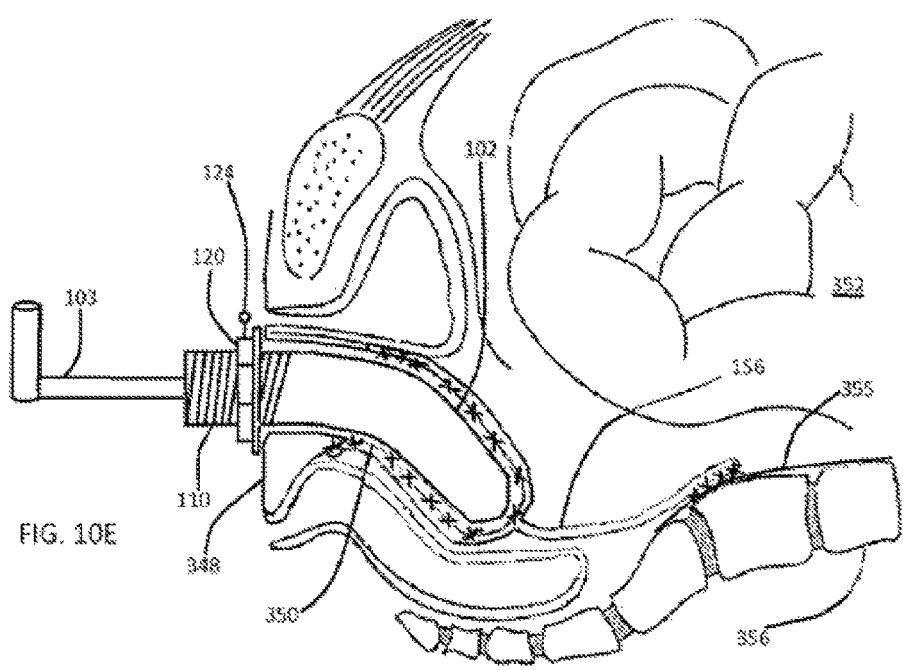

Still referring to FIG. 10d, once the two branches of the Y-shaped graft 156 have been secured to the vagina 350, the third branch (rolled up in FIG. 10d) of the Y-shaped graft 156 is unrolled in preparation for suturing to the anterior longitudinal ligament 355 overlying the sacral promontory 356. As illustrated in FIG. 10e, the vaginal probe manipulator apparatus can aid the surgeon to position the tissues to the desired tension and location within the pelvis, prior to suturing the proximal graft to the anterior longitudinal ligament 355. Once the proper position and tension is obtained as determined by the surgeon, then the suturing is done with laparoscopic instruments that are positioned in the abdominal cavity 352 and thus have access to the internal walls of the vagina and anterior longitudinal ligament 355 overlying the sacral promontory. Once the suturing is completed, as illustrated in FIG. 10e, the various laparoscopic instruments are removed and the insufflation gas is allowed to escape from the abdominal cavity 352. The vaginal manipulator probe 102 is removed from the patient.

While certain implementations have been described, other implementations are possible.

While FIGS. 10a-10e illustrate a sacrocolpopexy during which a vagina 350 is secured to the anterior longitudinal ligament 355 overlying the sacral promontory 356 of the patient, the vagina 350 can alternatively or additionally be attached via the graft 156 or a differently sized and/or shaped graft to other tissue or bone to correct the uterovaginal prolapse. For example, the vagina 350 can be secured to strong tissue in the pelvis of the patient. Alternatively or additionally, the vagina can be secured to the uterosacral and/or sacrospinous ligaments, or any other bony or ligamentous structure within the pelvis. During such procedures, the vaginal manipulator probe 102 is used in the same way to reposition the vagina 350 and assist in the dissection of the spaces between the vagina 350, the rectum 346, and the bladder 344, to provide the proper depth, position, and tension on the tissues, and to aid the suturing process.

Furthermore, referring to FIGS. 10a-10e, although the patient depicted in this demonstration has complete vaginal prolapse and is used to illustrate a function of the invention, the invention can also be used to treat less severe pelvic prolapse.

In addition, as an alternative to suturing the graft material to the vagina or cervix, the vagina or cervix may be directly sutured (without graft material) to the bony or ligamentous structures within the pelvis in some cases.

Figure 11:
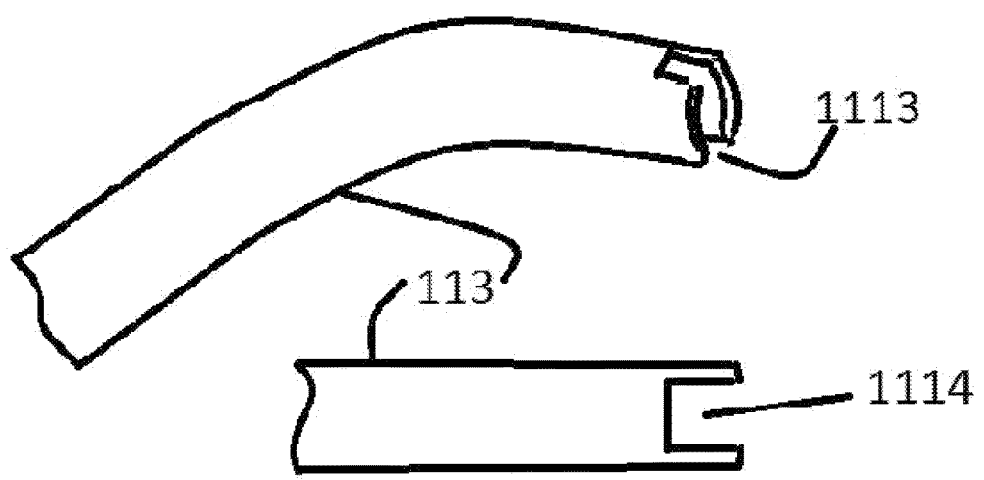
FIG. 11 is an exploded side and top view of one element of an embodiment.

While the vaginal manipulators described above have generally been used to secure the vagina in a patient whose uterus and/or cervix has been removed, vaginal manipulators can be used to reposition vaginas in patients who still retain their uterus and/or cervix. Such vaginal manipulator probes can contain a special end configuration slotted to receive a cervix during a procedure. FIG. 11 illustrates one vaginal manipulator probe with a slotted end 1113. As shown in FIG. 11 a distal end region 1113 of a probe 113 defines a slotted cut-out 1113 that extends proximally from the distal end surface of probe 113 and is configured to receive a cervix. The slotted recess has a width of about 2 cm to about 5 cm (e.g., about 4 cm) and a depth longitudinally of about 0.5 cm to about 5 cm (e.g., about 3.5 cm). The probe 113 can otherwise have dimensions similar to the probe 102 described above, and can be formed of any of the materials described above with respect to the probe assembly 100, described above.

Figure 12:
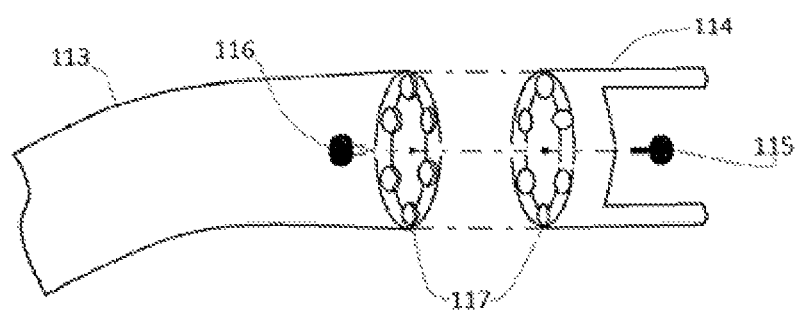
FIG. 12 is a diagrammatic perspective view of one element variation of an embodiment.

FIG. 12 further illustrates that certain embodiments of vaginal manipulator probes can contain a special distal end with a pivotable configuration slotted to receive a cervix during a procedure. FIG. 12 illustrates one vaginal manipulator probe with a slotted end 114. As shown in FIG. 12, a distal end region 114 of a probe 113 defines a slotted cut-out 114 that extends proximally from the distal end surface of probe 113 and is configured to receive a cervix. The slotted recess 114 has a width of about 2 cm to about 5 cm (e.g., about 4 cm) and a depth longitudinally of about 0.5 cm to about 5 cm (e.g., about 3.5 cm). The probe 113 distal end 114 is also configured to pivot about a central axis of a male stem piece 115 which couples with the female flared stem-lock 116 to secure the opposing rotating surfaces 117 whose opposing surfaces are substantially secured in the selected position by friction of the male stem piece 115 when pushed into the female stem lock 116 receiver in the central axis, and by the half sphere protrusions circumferentially positioned on the end of the probe body 113 and the corresponding half-sphere recesses on the inner surface of the distal tip configured to receive the half sphere protrusions of the probe body 113, with these surfaces substantially adjacent one to the other at interface 117 such that no appreciable gap is present. The protrusions are circular, about 2 mm to about 10 mm in diameter (e.g., about 5 mm) and protrude from the surface of the probe 113 distal tip at interface 117 for a maximum distance of about 1 mm to about 5 mm (e.g., about 2 mm), and the distal probe pivotable slotted tip 114 is configured on the proximal interface 117 with circular recesses positioned to receive the protrusions described above on the distal probe 113 at the interface 117 and of similar dimension to be substantially adjacent such that the probe tip 114 is pivotable for surgeon adjustment to the desired position and inhibit further movement once positioned. The surgeon can determine the correct orientation of the slotted probe tip 114 to receive a cervix. The probe 113 can otherwise have dimensions similar to the probe 102 described above and can be formed of any of the materials described above with respect to the probe assembly 100 described above.

Some embodiments of vaginal manipulator probes can be configured to receive a cervix during a procedure. FIG. 13 illustrates an implementation with the cervix 351 typically positioned in the neutral position as in 1314. In certain implementations, excess posterior vaginal wall length may be present (e.g., rectocele) after the vagina 350 with cervix 351 has been moved to the desired position with the vaginal manipulator probe 113 during a procedure to correct prolapse. In some implementations, the surgeon can shorten the posterior vaginal wall as in 1315 by repositioning the cervix 351 along the plane of the anterior wall without repositioning the vaginal probe manipulator during a sacrocolpopexy procedure, which can be advantageous in saving time and effort on the part of the surgeon. Furthermore, reorienting the cervix 351 in such a way can reduce or eliminate the need for additional surgical procedures (e.g., posterior colporrhaphy) of the vaginal walls after completion of the sacrocolpopexy, which can be advantageous on the part of the surgeon and the patient.

Still referring to FIG. 13, in certain implementations, excess anterior vaginal wall length may be present (e.g., cystocele) after the vagina with cervix has been moved to the desired position with the vaginal manipulator probe 113 during a procedure to correct prolapse. In some implementations, the surgeon can shorten the anterior vaginal wall as in 1316 by repositioning the cervix 351 along the plane of the posterior wall without repositioning the vaginal probe manipulator during a sacrocolpopexy procedure, which can be advantageous in saving time and effort on the part of the surgeon. Furthermore, reorienting the cervix in such a way can reduce or eliminate the need for additional surgical procedures (e.g., anterior colporrhaphy) of the vaginal walls after completion of the sacrocolpopexy, which can be advantageous on the part of the surgeon and the patient.

Figure 14:
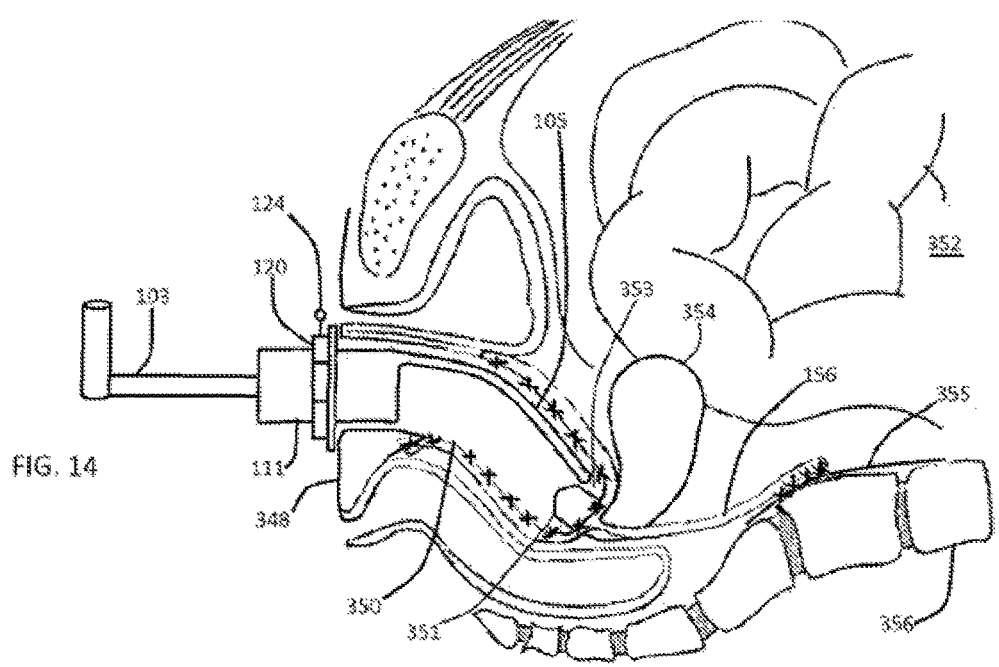
FIG. 14 is a diagrammatic sectional view of an embodiment variation in use.

In certain implementations, as illustrated in FIG. 14, a vaginal manipulator probe 105 is inserted fully into a vagina 350. As shown, a cervix 351 of the patient has been received adjacent to the bladed end of the probe 105, in the vaginal fornix 353. This allows the vaginal manipulator probe 105 to be maneuvered in a way to reposition the prolapsed vagina 350, cervix 351, and uterus 354 to its desired position without being hindered by the presence of the cervix 351. The curve and length of the vaginal manipulator probe 105 can help reduce the need for repositioning the vaginal manipulator probe 105 during the procedure. The adjustable disc 120 can be positioned against the perineal body 348 to substantially inhibit the escape of abdominal insufflation gas from the patient via her vagina 350 and to elevate the perineal body 348 to facilitate suture placement into the perineal body 348 for support of the pelvic floor, and to limit the insertion depth of the vaginal probe 105 to that depth predetermined by the surgeon to closely match the length of the vagina 350.

Figure 15:
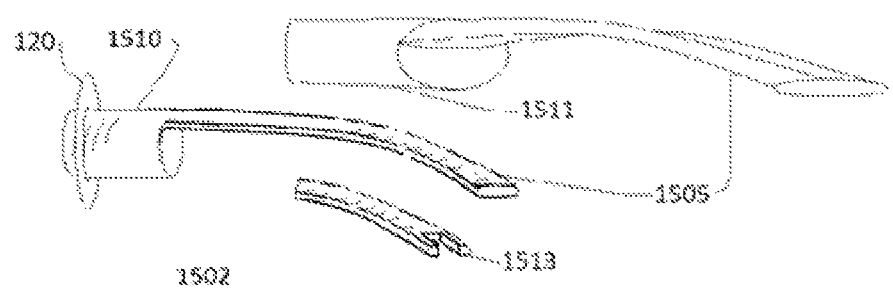
FIG. 15 is a perspective schematic view of one element of an embodiment variation.

While the bodies of certain embodiments of the vaginal manipulator probes described above are generally cylinders curved about their long axis, vaginal manipulator probe bodies can be of various other shapes. Referring to FIG. 15, for example, a vaginal manipulator probe 1502 includes a cylindrical proximal portion 1510 which can be threaded to receive the threaded adjustable disc 120, and a distal portion 1505 in a flattened oval cross section with the widest portion in the transverse plane when inserted in a vagina. The vaginal manipulator probe 1502 can be configured with a slotted recess 1513 at the distal end to receive a cervix.

Some embodiments of vaginal manipulator probe bodies described above can have threaded proximal portions configured to correspond to the threaded bore of an adjustable disc. Vaginal manipulator probes described above can also have a smooth proximal surface configured to correspond to the smooth bore 122 of an adjustable disc, as illustrated in FIG. 2a.

Figure 16:
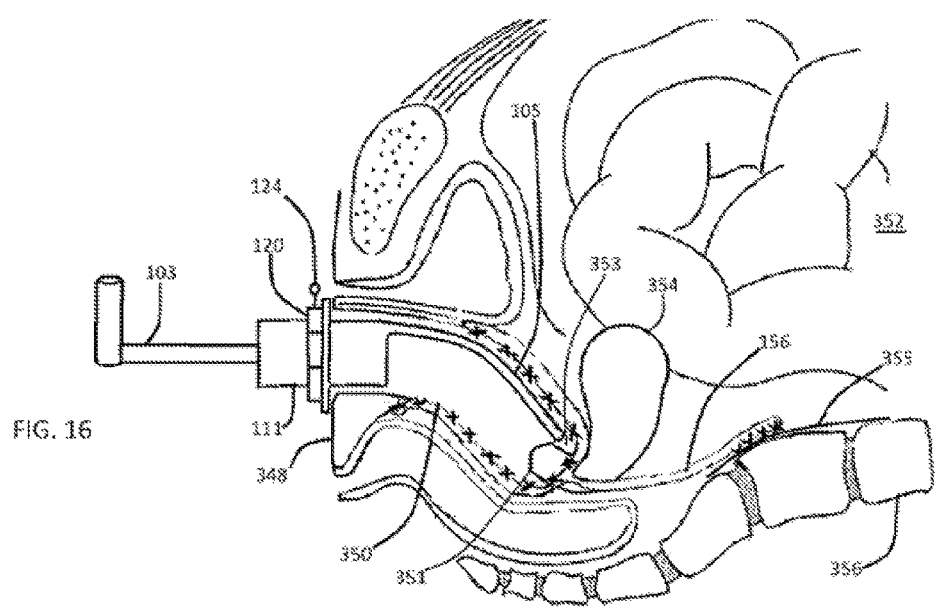
FIG. 16 is a perspective sectional view demonstrating an embodiment variation in use.

As illustrated in FIG. 16, in certain configurations of the vaginal manipulator probe 105, the distal portion extends from the proximal portion as a single thin blade, curved along its long axis to conform to the natural contours of a vagina 350, and can be used in much the same way as the vaginal manipulator probe 102 described above. For example, the vaginal manipulator probe 105 can be inserted into a prolapsed vagina 350, and the vaginal manipulator probe 105 can be used to reposition the vagina 350 into the desired position, orientation and depth in the patient. As the distal end of the vaginal manipulator probe 105 is inserted into a vagina 350 and approaches the cervix 351, the probe's single curved blade can be positioned in the anterior or posterior vaginal fornix 353, adjacent to the cervix 351. This allows the surgeon to fully advance the vaginal manipulator probe 105 until the vagina 350, cervix 351 and perineal body 348 are properly positioned relative to each other, and the proper depth adjustment is then set with the adjustable disc 120, which is positioned adjacent to the perineal body 348. The curved vaginal manipulator probe 105 distal surfaces then substantially contact the anterior and posterior vaginal walls, facilitating the repositioning to their normal anatomic position, facilitating the surgical dissection of the spaces for graft placement (e.g., rectovaginal space, vesicovaginal space) and providing a backstop for suture placement. The thin bladed distal end of the vaginal manipulator probe 105 allows the cervix 351 to be repositioned independently of the anterior and posterior vaginal walls without repositioning the vaginal probe manipulator 105. This allows the surgeon to shorten the length of the anterior or posterior vaginal walls by the width of the cervix 351, substantially reducing excess vaginal length of the anterior or posterior vaginal wall as determined by the surgeon. This can be advantageous in saving time and effort on the part of the surgeon. Furthermore, reorienting the cervix 351 in such a way can reduce or eliminate the need for additional surgical repairs (anterior or posterior colporrhaphy) of the vaginal walls after completion of the sacrocolpopexy, which can be advantageous on the part of the surgeon and the patient. The adjustable disc 120 can be positioned against the perineal body 348 to substantially inhibit the escape of abdominal insufflation gas from the patient via her vagina 350 and to elevate the perineal body 348 to facilitate suture placement into the perineal body 348 for support of the pelvic floor.

Figure 17:
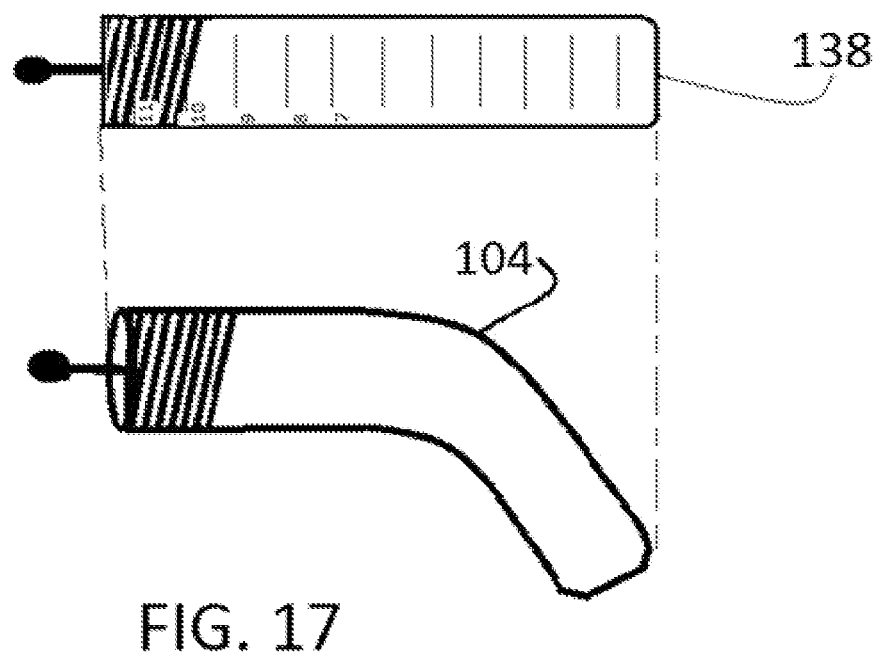
FIG. 17 is a top and side view demonstrating one element of an embodiment.

As illustrated in FIG. 17, certain embodiments of the vaginal manipulator probes can have measurement markings along the length of the probe body 104 to assist the surgeon with obtaining the proper vaginal insertion depth, as illustrated in the top view 138. The surgeon can measure the vaginal length prior to the surgical procedure (e.g., preoperatively in the office setting) or during the surgical procedure, to determine the most advantageous position and tension of the vagina, which can approximate the position to be obtained during the surgical procedure. The prolapsed pelvic organs can be repositioned and measured preoperatively in the office to approximate the anticipated surgical outcome, assisting the patient and the surgeon in understanding the most comfortable and acceptable position and tension of the repositioned vagina, cervix and uterus, if present. Alternatively, these measurements can be obtained in the surgical setting while the patient is under anesthesia, thereby allowing the surgeon to obtain the measurements, and then direct the assistant or other user of the vaginal manipulator probe as to the desired depth of insertion utilizing the measurement markings located on the vaginal manipulator probe 104 as reference. The vaginal depth measurements and position assessment can then be utilized as an approximation of the desired vaginal depth and position to be sought during the performance of a pelvic reconstruction procedure, such as sacrocolpopexy. The steps of pre-procedure measurement and position assessments can be advantageous for the surgeon to communicate to another person who is performing the actual positioning of the vaginal manipulator probe 104 during a pelvic reconstructive procedure, such that the position of the pelvic organs approximates that position which is expected and desired by the patient and surgeon, and can then be secured in the appropriate position, improving efficiency and accuracy.

Multiple different sized vaginal manipulator probes and different sized adjustable discs of any of the various types described above can be included in a kit. The kit can also provide the vaginal manipulator probe elongate shaft and handle. Prior to treatment, the surgeon can select the appropriate sized vaginal manipulator probe and adjustable disc that most closely matches the size of the vagina to be treated, and can then use that vaginal manipulator probe and adjustable disc during the vaginal prolapse surgical correction procedure. Selecting a vaginal manipulator probe that closely matches the size and length of the patient's vagina improves the ability of the surgeon to reposition the vagina after the vaginal manipulator probe has been inserted into the vagina and to provide the desired tension on the tissues and the desired position within the pelvis, to provide a backstop support to facilitate suturing of the different regions of the vagina, perineal body and cervix, and to inhibit the escape of abdominal insufflation gas from the patient's abdomen via the vagina during laparoscopy.

While some embodiments of the vaginal manipulator probes have been described as being affixed to the elongate shaft and handle, the vaginal manipulator probe may alternatively be affixed to other types of vaginal manipulator shafts.

While some embodiments of the vaginal manipulators have been described as being used during laparoscopic procedures to treat vaginal, uterovaginal and pelvic floor prolapse, they can also be used during open laparotomy procedures to correct vaginal, uterovaginal and pelvic floor prolapse.

While some embodiments of the vaginal prolapse correction procedures described above involve the surgeon grasping and maneuvering the vaginal manipulator probe, elongate shaft and handle in order to reposition the patient's vagina, an automated or remote-controlled device such as a robotic arm, can alternatively be used to grasp and maneuver the vaginal manipulator probe to reposition the patient's vagina.

While the vaginal manipulator probes above have been described as being used during vaginal prolapse correction procedures, the vaginal manipulators can be used for other types of procedures, such as laparoscopic procedures, including hysterectomy, removal of adnexal structures, excision of endometriosis, paravaginal defect repair, myomectomy and other gynecologic diagnostic and therapeutic procedures. These probes can also be used for gynecologic procedures done at laparotomy.

While the vaginal manipulator probes described above can be used in gynecologic procedures, they can be used also in general surgery procedures, including laparoscopic procedures and laparotomy procedures, and recto-sigmoid prolapse correction procedures.

Other implementations are within the scope of the following claims.

While the invention has been described in connection with these embodiments, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. An apparatus comprising:
a vaginal manipulator probe that includes a substantially rigid arcuate body portion including a substantially cylindrical or oval proximal portion and a blade-like distal portion that includes a recess configured to receive at least a portion of a cervix and that is curved along its long axis, the substantially rigid body portion being at least partially insertable into a vagina of a patient;
a disk rotatably coupled with the substantially rigid arcuate body portion of the vaginal manipulator probe and adjustable to one or more positions along a length of the substantially rigid arcuate body portion, the disk configured to rest against a perineal body of the patient when the substantially rigid arcuate body portion of the vaginal manipulator probe is inserted into the vagina of the patient to form a substantially fluid-tight seal against the patient, the disk also configured to set vaginal insertion depth of the substantially rigid arcuate body portion of the vaginal manipulator probe and allow rotation of the vaginal manipulator probe while maintaining the vaginal insertion depth; and
a handle portion operably coupled to the substantially rigid arcuate body portion of the vaginal manipulator probe that is configured to be external to the patient when the substantially rigid arcuate body portion of the vaginal manipulator probe is at least partially inserted into the vagina of the patient.

2. The apparatus of claim 1, wherein the handle portion is rotatable to one or more different positions relative to the substantially rigid arcuate body portion of the vaginal manipulator probe.

3. The apparatus of claim 1, wherein the disk is adjustable and movably lockable to one or more positions along a length of the substantially rigid arcuate body portion of the vaginal manipulator probe.

4. The apparatus of claim 3, wherein the vaginal manipulator probe further comprises a threaded nut disposed on a threaded portion of the substantially rigid arcuate body portion of the vaginal manipulator probe.

5. The apparatus of claim 3, wherein the disk includes a prominence configured to slide within a channel disposed within the substantially rigid arcuate body portion of the vaginal manipulator probe to align the disk relative to the substantially rigid arcuate body portion of the vaginal manipulator probe.

6. The apparatus of claim 1, wherein the substantially rigid arcuate body portion of the vaginal manipulator probe includes a distal rotatable tip portion.

7. The apparatus of claim 1, wherein the substantially rigid arcuate body portion of the vaginal manipulator probe includes one or more measurement markings along at least a portion of its length.

8. The apparatus of claim 1, wherein the substantially rigid arcuate body portion of the vaginal manipulator probe includes a distal tip portion that is smooth.

9. The apparatus of claim 1, wherein the substantially rigid arcuate body portion of the vaginal manipulator probe includes a removable distal tip portion.

10. The apparatus of claim 1, wherein the disk is in a shape of an oval, circle, or tear-drop.

11. An apparatus comprising:
- a vaginal manipulator probe that includes a substantially rigid arcuate body portion being curved along its long axis and having an oval cross-sectional shape, the substantially rigid body portion including one or more measurement markings along at least a portion of its length and being at least partially insertable into a vagina of a patient;
- a disk rotatably coupled with the substantially rigid arcuate body portion of the vaginal manipulator probe and adjustable to one or more positions along a length of the substantially rigid arcuate body portion, the disk configured to rest against a perineal body of the patient when the substantially rigid arcuate body portion of the vaginal manipulator probe is inserted into the vagina of the patient to form a substantially fluid-tight seal against the patient, the disk also configured to set vaginal insertion depth of the substantially rigid arcuate body portion of the vaginal manipulator probe and allow rotation of the vaginal manipulator probe while maintaining the vaginal insertion depth; and
- a handle portion operably coupled to the substantially rigid arcuate body portion of the vaginal manipulator probe that is configured to be external to the patient when the substantially rigid arcuate body portion of the vaginal manipulator probe is at least partially inserted into the vagina of the patient.

12. The apparatus of claim 11, wherein the substantially rigid arcuate body portion includes a substantially cylindrical proximal portion and a blade-like distal portion that includes a recess configured to receive at least a portion of a cervix.

13. The apparatus of claim 11, wherein the handle portion is rotatable to one or more different positions relative to the substantially rigid arcuate body portion of the vaginal manipulator probe.

14. The apparatus of claim 11, wherein the disk is adjustable and movably lockable to one or more positions along a length of the substantially rigid arcuate body portion of the vaginal manipulator probe.

15. The apparatus of claim 14, wherein the vaginal manipulator probe further comprises a threaded nut disposed on a threaded portion of the substantially rigid arcuate body portion of the vaginal manipulator probe.

16. The apparatus of claim 14, wherein the disk includes a prominence configured to slide within a recess disposed within the substantially rigid arcuate body portion of the vaginal manipulator probe to align the disk relative to the substantially rigid arcuate body portion of the vaginal manipulator probe.

17. The apparatus of claim 11, wherein the substantially rigid arcuate body portion of the vaginal manipulator probe includes a distal rotatable tip portion.

18. The apparatus of claim 11, wherein the substantially rigid arcuate body portion of the vaginal manipulator probe includes a distal tip portion that is smooth.

19. The apparatus of claim 11, wherein the substantially rigid arcuate body portion of the vaginal manipulator probe includes a removable distal tip portion.

20. The apparatus of claim 11, wherein the disk is in a shape of an oval, circle, or tear-drop.

* * * * *